US010535159B2

United States Patent
Koizumi et al.

(10) Patent No.: US 10,535,159 B2
(45) Date of Patent: Jan. 14, 2020

(54) IN VIVO MOTION TRACKING DEVICE AND IN VIVO MOTION TRACKING METHOD

(71) Applicants: The University of Electro-Communications, Tokyo (JP); PUBLIC UNIVERSITY CORPORATION YOKOHAMA CITY UNIVERSITY, Kanagawa (JP)

(72) Inventors: Norihiro Koizumi, Tokyo (JP); Yu Nishiyama, Tokyo (JP); Ryosuke Kondo, Tokyo (JP); Kyohei Tomita, Tokyo (JP); Fumio Eura, Tokyo (JP); Kazushi Numata, Yokohama (JP)

(73) Assignees: The University of Electro-Communications, Tokyo (JP); PUBLIC UNIVERSITY CORPORATION YOKOHAMA CITY UNIVERSITY, Kanagawa (JP)

( * ) Notice: Subject to any disclaimer, the term of this patent is extended or adjusted under 35 U.S.C. 154(b) by 148 days.

(21) Appl. No.: 15/867,302

(22) Filed: Jan. 10, 2018

(65) Prior Publication Data

US 2019/0057517 A1 Feb. 21, 2019

(30) Foreign Application Priority Data

Aug. 18, 2017 (JP) ................ 2017-158071

(51) Int. Cl.
*G06T 7/73* (2017.01)
*A61B 8/08* (2006.01)
*G06T 7/40* (2017.01)

(52) U.S. Cl.
CPC .............. *G06T 7/74* (2017.01); *A61B 8/085* (2013.01); *A61B 8/5215* (2013.01); *A61B 8/5276* (2013.01); *G06T 7/40* (2013.01); *G06T 2207/10132* (2013.01); *G06T 2207/20081* (2013.01); *G06T 2207/30096* (2013.01)

(58) Field of Classification Search
CPC ... G06T 7/74; G06T 7/40; G06T 2207/10132; G06T 2207/30096; G06T 2207/20081; A61B 8/5276; A61B 8/085; A61B 8/5215
USPC .......................................... 382/103
See application file for complete search history.

(56) References Cited

FOREIGN PATENT DOCUMENTS

JP A-2016-158890 9/2016
WO WO-2016139832 A1 * 9/2016 ............... A61B 8/08

OTHER PUBLICATIONS

S.C.Davies, A.L.Hill, R.B.Holmes, M.Halliwell, and P.C.Jackson, "Ultrasound quantitation of respiratory organ motion in the upper abdomen," The British Journal of Radiology, 1994.

(Continued)

*Primary Examiner* — Amandeep Saini
(74) *Attorney, Agent, or Firm* — Meunier Carlin & Curfman LLC

(57) ABSTRACT

An in vivo motion tracking device tracking an in vivo motion that is a tracking target included in an ultrasonic image includes an image acquiring unit that is configured to acquire an ultrasonic image, an advance learning unit that is configured to perform advance learning using the ultrasonic image as learning data, and a tracking unit that is configured to track a position of the tracking target in an ultrasonic image including the tracking target after the advance learning performed by the advance learning unit.

8 Claims, 20 Drawing Sheets

(56) References Cited

OTHER PUBLICATIONS

M.A.Clifford, F.Banovac, E.Levy, and K.Cleary, "Assessment of hepatic motion secondary to respiration for computer assisted interventions," Computer Aided Surgery, 2002.
D.R.Daum, N.B.Smith, and et al., "In vivo demonstration of non-invasive thermal surgery of the liver and kidney using an ultrasonic phased array," Ultrasound in Med.& Biol., 1999.
C.E.Kleynen, B.J.Slotman, F.J.Lagerwaard, J.R.v.S.d.Koste, S.Senan, "Renal mobility during uncoached quiet respiration: an analysis of 4dct scans," International Journal of Radiation Oncology & Biology & Physics, 2006.
M.Feron, B.Bussels and L.Goethals, "Respiration-induced movement of the upper abdominal organs: a pitfall for the three-dimensional conformal radiation treatment of pancreatic cancer," Radiotherapy and Oncology, 2003.
D. Pham, T. Kron, F. Foroudi, M. Schneider, S. Siva, "A Review of Kidney MotionUnder Free, Deep and Forced-shallow Breathing Conditions: Implications for Stereotactic Ablative Body Radiotherapy Treatment," Technology in Cancer Research& Treatment 2013, 2013.
T. Toyoda, "Texture Classification Using Extended Higher Order Local Autocorrelation Features," Proceedings of the 4th International Workshop on Texture Analysis and Synthesis, 2005.
Kenji Iwata et al., Toward Building Cancer Pathological Image Diagnosis Supporting System Using Higher-order Local Autocorrelation Feature Method(HLAC), The Japanese Society of Medical Imaging Technology Conference Proceedings, 2009.
Henriques, J. F., Caseiro, R., Martins, P., & Batista, J. High-Speed Tracking with Kernelized Correlation Filters. IEEE Transactions on Pattern Analysis and Machine Intelligence (TPAMI) 37 (3), 583-596.
Ryosuke Kondo et al., 1A1-L04, An ultrasound guided tracking method for a tumor utilizing HLAC based dynamic template matching, No. 17-2 Proceedings of the 2017JSME Conference on Robotics and Mechatronics, Fukushima, Japan, May 10-13, 2017.
Ryosuke Kondo et al., 2017 14th International Conference on Ubiquitous Robots and Ambient Intelligence (URAI) Jun. 28-Jul. 1, 2017 at Maison Glad Jeju, Jeju, Korea.
T. Kihara et al., "Registration of 4D Ultrasound Images and its Applications," The Japanese Society of Medical Imaging Technology, 2010. (English abstract only).
T. Kihara et al., "GPU Computation of Local Features Derived from 3D-localStatistics" Medical Imaging Technology vol. 31 No. 5 Nov., 2013. (English abstract only).
K. Kishi et al., "Compact Manipulator System for Guiding Needle with Real-time Navigation Based on MR Images", J JSCAS, 2007.
Y. Ryo et al., "Motion Analysis of Ultrasound Image Based on Optical Flow and Texture Information," IEICE Technical Report, IMQ 113 (468), 2014.
Yudai Yamazaki, Masaya Iwata et al., "Anomaly Detection from Breast Ultrasound Images Using AdaBoost Based on Higher-order Local Autocorrelation Feature", Research Report Mathematical Modeling and Problem Solving (MPS),Information Processing Society of Japan, 2012. (English abstract only).
Ryosuke Kondo, Norihiro Koizumi, Graduation thesis, Study on Improvement of Trajectory Accuracy in Ultrasound Guided RFA Treatment Support System, 2017.

\* cited by examiner

ZERO DIMENSION

ONE DIMENSION

TWO DIMENSIONS

3 × 3      5 × 5

IN VIVO MOTION TRACKING DEVICE AND IN VIVO MOTION TRACKING METHOD

CROSS-REFERENCE TO RELATED APPLICATION

This application claims priority to and benefit of Japanese Patent Application No. 2017-158071 filed on Aug. 18, 2017, which is hereby incorporated by reference in its entirety.

BACKGROUND OF THE INVENTION

Field of the Invention

The present disclosure relates to an in vivo motion tracking device and an in vivo motion tracking method for tracking a focused portion moving inside a living body.

Description of Related Art

Conventionally, an in vivo motion tracking device that tracks a focused part moving almost periodically inside a living body in a living body image acquired by imaging a living body structure is known (for example, see Patent Document 1). In the in vivo motion tracking device described in Patent Document 1, a characteristic information learning unit learns characteristic information representing characteristics of a living body image inside a focused area corresponding to a focused part using the living body image in a focused part motion period preceding this tracking process and generates tracking characteristic information. A tracking processing unit acquires the position of a focused part by searching a focused area on the basis of tracking characteristic information in a living body image that changes in time. In addition, a reference setting means sets a reference focused area at a position that is a reference position on a trajectory of the focused area. A characteristic information generating means extracts reference characteristic information that is characteristic information of the inside of the reference focused area, acquires a trajectory by tracking a focused area according to the reference characteristic information, and acquires tracking characteristic information in association with a position on the trajectory using the characteristic information extracted from the tracked focused area.

[Patent Document 1] Japanese Unexamined Patent Application, First Publication No. 2016-158890

However, when the in vivo motion tracking device described in Patent Document 1 is used, for example, when an operator such as a doctor or an inspection technician tracks a focused part (tracking target), it is necessary for the operator to operate an input unit (for example, a keyboard, a pointing device, or the like) and designate a reference focused area on a living body image while viewing the living body image, for example, displayed on a display unit. In such a case, the operator needs to select reference characteristic information that is appropriate for tracking in which the characteristics of the focused area appropriately appear. In more detail, at a timing at which an image pattern that is appropriate for tracking a focused part appears in an ultrasonic image, the operator needs to set an image area including the image pattern as a reference focused area.

In other words, when the in vivo motion tracking device described in Patent Document 1 is used, the operator needs to manually perform a mapping operation of a tracking target position. In addition, when the in vivo motion tracking device described in Patent Document 1 is used, since the mapping operation of the tracking target position is manually performed by the operator, the operator performs only a tracking target position determining process for a small amount of data and cannot perform a fast tracking target position determining process of a large amount of data.

SUMMARY OF THE INVENTION

The present disclosure is in consideration of the situation described above, and an object thereof is to provide an in vivo motion tracking device and an in vivo motion tracking method capable of quickly performing a tracking target position determining process for a large amount of data without requiring a manual mapping operation of a tracking target position.

According to the present disclosure, there is provided an in vivo motion tracking device tracking an in vivo motion that is a tracking target included in an ultrasonic image including: an image acquiring unit that is configured to acquire an ultrasonic image; an advance learning unit that is configured to perform advance learning using the ultrasonic image as learning data; and a tracking unit that is configured to track a position of the tracking target in an ultrasonic image including the tracking target after the advance learning performed by the advance learning unit, wherein the advance learning unit includes: a learning template processing part that is configured to perform a template process using the ultrasonic image of the learning data; an area extracting part that is configured to extract an area included in the ultrasonic image of the learning data; a learning texture analyzing part that is configured to perform a texture analysis of the area extracted by the area extracting part; and a main component analyzing part that is configured to perform a main component analysis of a result of the texture analysis performed by the learning texture analyzing part, and wherein the tracking unit includes: a tracking texture analyzing part that is configured to perform a texture analysis of the ultrasonic image including the tracking target; a template automatic selecting part that is configured to select an image area that is appropriate for tracking the tracking target as a template on the basis of a result of the texture analysis performed by the tracking texture analyzing part and a result of the learning performed by the advance learning unit; a tracking template processing part that is configured to perform an update-type template process for each of a plurality of templates that are sequentially selected by the template automatic selecting part; and a tracking target position determining part that is configured to determine a position having a highest degree of correlation as the position of the tracking target on the basis of a result of the template process for the plurality of templates performed by the tracking template processing part.

In the in vivo motion tracking device according to the present disclosure, the tracking unit may further include a position correcting part that is configured to perform position correction according to an initial template having no accumulated error, and the position correcting part, when matching for the initial template has a degree of correlation of a fixed value or more, may correct the position of the tracking target to a position of the tracking target at that time point.

In the in vivo motion tracking device according to the present disclosure, the tracking unit may further include a monitoring part that constantly monitors a region of interest, and the monitoring part may include: a region setting part that is configured to set a template of an initial region of interest; a calculation part that is configured to, after tracking, calculate the distance between the template of the initial region of interest set by the region setting part and a region of interest that is currently being tracked; a determination part that is configured to determine whether or not the distance calculated by the calculation part exceeds a predetermined threshold; and a notification part that is configured to perform notification with an alarm when the distance calculated by the calculation part exceeds the predetermined threshold.

In the in vivo motion tracking device according to the present disclosure, when the distance calculated by the calculation part exceeds the predetermined threshold, the notification part may perform notification with the alarm and store an image of a corresponding region of interest in a database in a readable form.

In the in vivo motion tracking device according to the present disclosure, the learning template processing part may perform template matching using the ultrasonic image of the learning data, and the tracking template processing part may perform update-type template matching.

In the in vivo motion tracking device according to the present disclosure, the learning template processing part may perform Kernerlized correlation filters (KCF) tracking using the ultrasonic image of the learning data, and the tracking template processing part may perform the KCF tracking.

The in vivo motion tracking device according to the present disclosure may be an in vivo motion tracking device for supporting an ultrasound-guided radio frequency ablation (RFA) treatment or a high intensity focused ultrasound (HIFU) treatment.

According to the present disclosure, there is provided an in vivo motion tracking method for tracking an in vivo motion that is a tracking target included in an ultrasonic image including: acquiring an ultrasonic image; performing advance learning using the ultrasonic image as learning data; and tracking a position of the tracking target in the ultrasonic image including the tracking target after performing the advance learning in the performing of the advance learning, wherein the performing of the advance learning includes: performing a template process using the ultrasonic image of the learning data; extracting an area included in the ultrasonic image of the learning data; performing a texture analysis of the area extracted in the extracting of an area; and performing a main component analysis of a result of the texture analysis performed in the performing of the texture analysis, and wherein the tracking of the position of the tracking target includes: performing a texture analysis of the ultrasonic image including the tracking target; selecting an image area that is appropriate for tracking the tracking target as a template on the basis of a result of the texture analysis performed in the performing of the texture analysis and a result of the learning performed in the performing of the advance learning; performing an update-type template process for each of a plurality of templates that are sequentially selected in the selecting of the image area; and determining a position having a highest degree of correlation as the position of the tracking target on the basis of a result of the template process for the plurality of templates performed in the performing of the update-type template process.

According to the present disclosure, an in vivo motion tracking device and an in vivo motion tracking method capable of quickly performing a tracking target position determining process for a large amount of data without requiring a manual mapping operation of a tracking target position can be provided.

DETAILED DESCRIPTION OF THE INVENTION

Before an in vivo motion tracking device and an in vivo motion tracking method according to embodiments of the present disclosure are described, treatments and the like to which the in vivo motion tracking device and the in vivo motion tracking method according to the present disclosure can be applied will be described.

In recent years, as a minimally invasive treatment, a radio frequency ablation (RFA) treatment is widely used as a treatment method for liver cancer. The RFA treatment is a treatment method in which tumors are cauterized by puncturing the tumors and discharging radio waves from a needle tip. When compared with an abdominal operation, the RFA treatment is relatively uninvasive and is an extremely effective surgical means for liver cancer that is ranked fifth in the number of deaths in terms of parts and is ranked sixth in morbidity.

Figure 1:
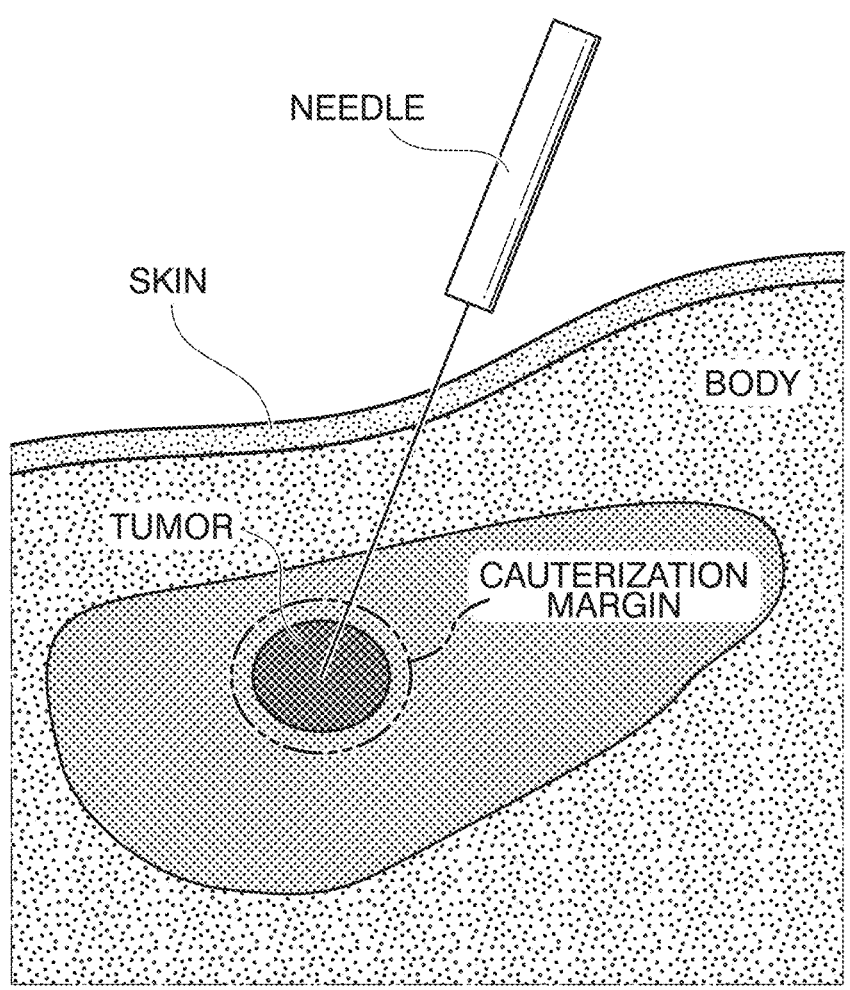
FIG. 1 is a diagram showing radio frequency ablation (RFA)

FIG. 1 is a diagram showing the RFA. As shown in FIG. 1, in an RFA treatment, a tumor is punctured, and radio waves are discharged to cauterize the tumor and a cauterization margin area on the periphery thereof. In order to observe the appearance of the peripheral portion of a tumor when the RFA treatment is performed, ultrasound-guided RFA, MR-guided RFA, or the like is performed. In addition, when a tumor is at a position that is difficult to observe, an ultrasonic imaging-guided RFA treatment or the like is also performed.

The RFA treatment is widely used as a minimally invasive treatment for liver cancer. As an essential element for minimally invasiveness, there is monitoring of a tumor. By continuously and correctly perceiving the positional relation of a tumor, a treatment only of a tumor can be accurately performed. By continuously and correctly perceiving the positional relation of a tumor, complete cauterization of a tumor part and a low invasiveness to non-tumor parts can be achieved.

When an in vivo motion tracking device and an in vivo motion tracking method according to embodiments of the present disclosure are applied to an RFA treatment supporting system, the RFA treatment supporting system performs superimposed display for a tumor and an analysis of luminance information of a tumor and the peripheral portion of the tumor. When this RFA treatment supporting system is operated, a tumor can be correctly followed constantly. An object of an in vivo motion tracking device and an in vivo motion tracking method according to embodiments of the present disclosure is to improve the tracking ability for an in vivo motion of a tumor and the like under conditions in which an actual operation environment is considered. The features of the in vivo motion tracking device and the in vivo motion tracking method according to embodiments of the present disclosure are as discussed below.

An in vivo motion in an acquired image is tracked with high accuracy.

An image area that is optimal for tracking is selected according to advance learning using a texture analysis.

By performing the texture analysis whenever necessary, the template image that is optimal for tracking is updated.

<Problem in RFA Treatment>

In an RFA treatment, the ratio of local recurrence is 2.1% to 16.5%, and it is necessary to completely cauterize liver cancer to improve the ratio of local recurrence. For this reason, it is necessary to cauterize a tumor and a cauterization marginal portion together.

It is necessary to perceive a treatment range of the RFA for complete cauterization. Meanwhile, when the treatment range is wide, a cauterization range with one puncture is insufficient, and it is necessary to perform a treatment by performing a plurality of punctures of one tumor part. At this time, when cauterization is performed once, a hyperechoic region is generated according to the cauterization to cover a tumor, and there is a problem in that determination of a next position to be punctured from an ultrasonic image is obstructed. For complete cauterization for preventing the recurrence, it is necessary to constantly perceive a correct position of a tumor part and perceive the treatment effect range thereof.

<Conventional Research for RFA Treatment Support>

Two examples will be described as research relating to RFA treatment support. One is research relating to treatment research relating to treatment support in the middle of an RFA treatment, and the other is a research relating to an RFA operation robot.

[Research Relating to Observation of RFA Treatment Using 4D Ultrasonic Image]

In a document by T. Kihara, "Registration of 4D Ultrasound Images and its Applications," The Japanese Society of Medical Imaging Technology, 2010, Kihara has proposed a technique for observation of an RFA treatment using 4D ultrasonic waves acquiring an ultrasonic image electrically and mechanically as three dimensional information. It is expected that acquisition of mutual positions of a lesioned part and a puncturing needle with high accuracy using a 4D ultrasonic image will lead to improvement of treatment outcomes. For this reason, position adjustment is performed according to the similarity of volume data of an anatomically characteristic part that is manually selected. Here, as characteristic positions, the diaphragm and blood vessels are used. Regarding the accuracy, since the purpose is for supporting doctors, accuracy according to measurement on the basis of a difference from correct coordinates is not used, and a doctor is allowed to determine whether there is a deviation, and the system performance is evaluated according to the determination.

In this research, the time resolution of volume data is five per one second. For this reason, the time resolution is low, and an error due to the low resolution is considered to occur. From that, it is considered to be necessary to acquire an ultrasonic moving image using a method having as high time resolution as possible. In addition, while a technique for performing tracking on the basis of the similarity for the volume data is used, it has a problem of a large amount of calculation.

In addition, a document by Tomohiko Kihara, "Increase in speed in calculating characteristic amounts on the basis of three-dimensional local statistical amounts using a GPU," MEDICAL IMAGING TECHNOLOGY Vol. 31 No. 5 November, 2013, Kihara and coauthors proposed implementation of a high speed using a GPU for increasing the calculation speed of this technique. According to such a technique, while the performance improvement of about 16 to 210 times is achieved, real time tracking is not currently realized. In addition, there is a problem in that the spatial resolution is currently low. Thus, in the future, new improvement of the calculation speed and an increase in the spatial resolution are necessary.

[Research Relating to Puncturing Support Using MR Image]

In a document by Kousuke Kishi, "Compact Puncturing Manipulator System Having MR Image Guiding Function," Japan Society of Computer-aided Surgery 2007, Kishi and coauthors performed research on a robot supporting an MR-guided RFA operation and research relating to tumor tracking in an MR image. For the liver having a large body motion as a target, a robot system in which the posture of a puncturing needle can be adjusted in accordance with the motion of the organ in real time has been built. Since an operation is performed under MRI, the robot is formed using a material that does not easily disturb a magnetic field. Regarding tracking, tracking of the position posture of the puncturing needle is performed on the basis of an optical three-dimensional position measuring device from the outside. In addition, a tumor is assumed to be manually tracked.

Here, tracking of a tumor is performed by a doctor by determining the position of the tumor on the basis of an MR image. Since capturing an MR image takes four seconds per section, it can be seen that the time is longer than a respiratory cycle. For this reason, as a compensation for motions of organs according to respiration and the like, the time resolution is considered to be insufficient.

Here, ultrasonic waves enable real-time imaging of 20 FPS or more and have time resolution that can respond also to the compensation for motions of organs according to respiration and the like.

<Tracking Motion in RFA Treatment Supporting System>

In an RFA treatment, there are factors obstructing doctor's treatments as described above. In the conventional research described in "Conventional research relating to RFA treatment support," tracking is determined on the basis of images acquired by a doctor.

On the other hand, in the in vivo motion tracking device and the in vivo motion tracking method according to embodiments of the present disclosure to be described later, the position is presented by tracking in vivo motion in an ultrasonic moving image.

Figure 2:
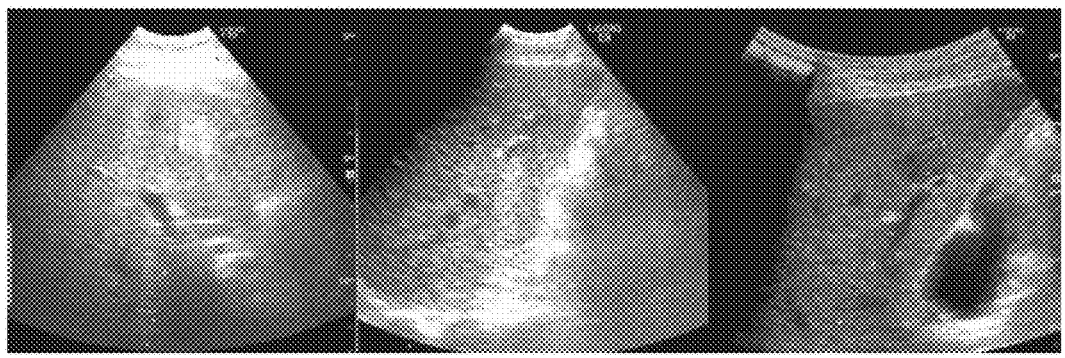
FIG. 2 shows diagrams showing examples of ultrasonic images in RFA cauterization therapy.

FIG. 2 shows diagrams showing examples of ultrasonic images in RFA cauterization therapy. In more detail, the left diagram in FIG. 2 shows an example in which the boundary of a liver area is clear. The middle diagram in FIG. 2 shows an example in which the boundary of a liver area is clear, and a diaphragm is seen. The right diagram in FIG. 2 shows an example in which the boundary of a liver area is unclear and the diaphragm is not seen. In this way, the actual operation environment of RFA has the following characteristics.

Ultrasonic moving images are captured in various scales.
Since the parts that are shown are different, there are cases in which the diaphragm is shown and cases in which the diaphragm is not shown. In addition, there are cases in which the boundary of the liver area is clear and cases in which the boundary of the liver area is unclear
Since showing is made on the basis of a probe gripped by a doctor, there are cases in which the probe is separated from the body surface or greatly moves.

According to this, in the in vivo motion tracking device and the in vivo motion tracking method according to embodiments of the present disclosure to be described below, a characteristic can be selected for each ultrasonic moving image and can be stored in the middle of the process, and tracking is performed according to template matching that can respond to the disturbance or disappearance of an ultrasonic moving image for a short time.

Next, the principle of template matching will be described.

Figure 3:
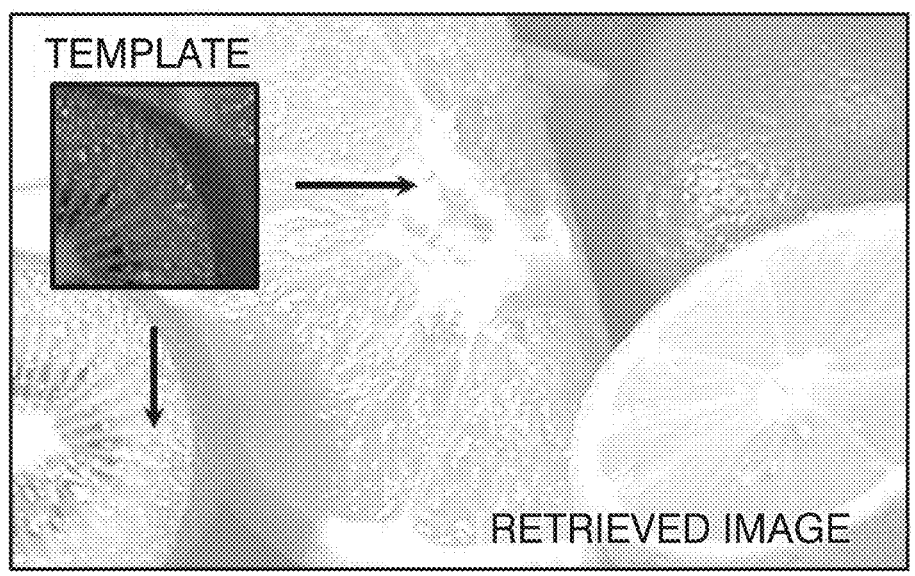
FIG. 3 is a diagram showing the principle of template matching.

FIG. 3 is a diagram showing the principle of template matching.

As shown in FIG. 3, the template matching is a technique for acquiring an image that is a tracking target in advance as a template and checking the similarity between the template and a retrieved image by comparing and collating the template and the retrieved image with each other through overlapping. The similarity is checked while the template is moved in an area in the retrieved image, and a position at which the similarity is the highest is detected. As a measure for the evaluation of the similarity, a sum of absolute differences (SAD) of luminance values, a sum of squared differences (SSD) of luminance values, a normalized correlation coefficient, or the like is used. In one example of the in vivo motion tracking device and the in vivo motion tracking method according to embodiments of the present disclosure to be described later, a normalized correlation coefficient that is robust for a linear transformation of luminance values of an image is employed.

Figure 4:
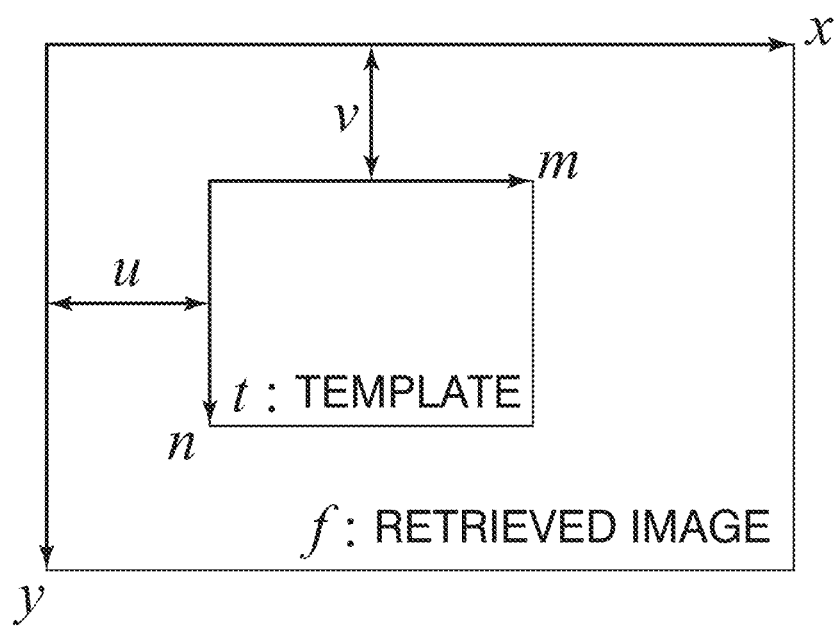
FIG. 4 is a diagram showing a coordinate system of a template and a retrieved image.

FIG. 4 is a diagram showing a coordinate system of a template and a retrieved image.

In the example shown in FIG. 4, a template t(m, n) (here, m=0 to M−1 and n=0 to N−1), and a retrieved image f(x, y) (here, x=0 to X−1, and y=0 to Y−1) are shown. A partial image having the same size (M×N) as the template having a point (u, v) as a start point in a retrieved image will be denoted by $f^{u,v}$. When the normalized correlation coefficient at this time is denoted by $R^{u,v}$, $R^{u,v}$ is given using Equation (1).

Here, $\bar{t}$ and $\bar{f}$ are respectively an average luminance value of the template and an average luminance value of a retrieved image and are respectively given using Equation (2) and Equation (3).

$$R^{u,v} = \frac{\sum_{m}^{M} \sum_{n}^{N} (f^{u,v}(m, n) - \bar{f}^{u,v})(t(m, n) - \bar{t})}{\sqrt{\sum_{m}^{M} \sum_{n}^{N} (f^{u,v}(m, n) - \bar{f}^{u,v})^2} \sqrt{\sum_{m}^{M} \sum_{n}^{N} (t(m, n) - \bar{t})^2}} \quad (1)$$

$$\bar{t} = \frac{\sum_{m}^{M} \sum_{n}^{N} t(m, n)}{M \times N} \quad (2)$$

$$\bar{f}^{u,v} = \frac{\sum_{m}^{M} \sum_{n}^{N} f^{u,v}(m, n)}{M \times N} \quad (3)$$

When a luminance value of an image is perceived as a vector in an M+N dimensional space, the normalized correlation coefficient corresponds to an inner product of two vectors in the M+N dimensional space. For this reason, the normalized correlation coefficient has a value of "1" when the correlation of the image is the highest and has a value of "−1" when the degree of correlation is the lowest.

<Motion Compensation for Ultrasonic Moving Image and Tracking Moving Image>

In recent years, research relating to motion compensation using tracking of ultrasonic moving images has been widely performed. When an ultrasonic diagnosis is compared with MR or CT that are other medical image technologies, there are the following characteristics.

- The time space resolution is superior.
- There is no invasiveness because there is no radiation exposure.
- Introduction can be easily performed at a low cost.
- Introduction can be easily performed without requiring a dedicated room or large machine.
- The ultrasonic diagnosis can be introduced in operation environments of various cases because the machines are small.
- The appearance of soft tissue and blood vessels, the appearance of blood flow, and the like can be checked in real time.
- On the other hand, in an ultrasonic image, noises called a white nose and a speckle noise specific to a tissue are present, and the ultrasonic image is an image of a section, and thus, there is a factor disturbing tracking such as a change in the texture accompanied with a change in the section.
- Since ultrasonic waves do not pass through hard tissue such as bones, an area that is not drawn called an acoustic shadow is generated.

In addition, when monitoring is performed using an ultrasonic image, a person's organs move according to respiration, a heartbeat, peristaltic motions of the intestines, arbitrary body motions, and the like. The maximum displacement of the liver is 24.4±16.4 mm, and it can be understood that the liver greatly moves. As above, there are advantages of easy introduction and high compatibility with diagnoses and treatments.

<Factors of Tracking Error and Conventional Research>

[Research Relating to Dynamic Analysis of Ultrasonic Image According to Optical Flow]

In a document by Y. Ryo, "Motion Analysis of Ultrasound Image According to Optical Flow and Texture Information," Institute of Electronics, Information and Communication Engineers Technical Research Report IMQ, Image Media Quality 113(468), 2014, Yokoyama and coauthors proposed a high-density dynamic analysis method for an ultrasonic image by following lattice points.

In the dynamic analysis method, lattice points are set on an ultrasonic image, detection of lattice points on the basis of a binary characteristic amount is performed for texture information, and tracking according to an optical flow on the basis of a result thereof is performed. Here, by introducing a multi-spring model in the points, the influence of noise is partially reduced, and the robustness is improved.

[Research Relating to Tracking of Lesioned Part Using Particle Filter on Ultrasonic Image]

In a document by S. C. Davies, A. L. Hill, R. B. Holmes, M. Halliwell, and P. C. Jackson, "Ultrasound quantitation of respiratory organ motion in the upper abdomen," The British Journal of Radiology, 1994, Marco Carletti and coauthors proposed a tracking technique using update template matching using a particle filter in tracking blood vessels in the liver in the same section. The accumulation of errors accompanied with the update of a template is tracked using a particle filter and updating a reference template according to the likelihood at that time and changing a spraying range of particles at the time of a displacement time for large displacement of a tracking target according to an abrupt body motion or the like. This uses a data set of CLUST 2015 of MICCAI. In this data set, the purpose is to track blood vessels in the liver in an ultrasonic image, and the appearance of motions according to the respiration of the liver in the same section is collected.

<Ultrasound-guided RFA Treatment>

Figure 5:
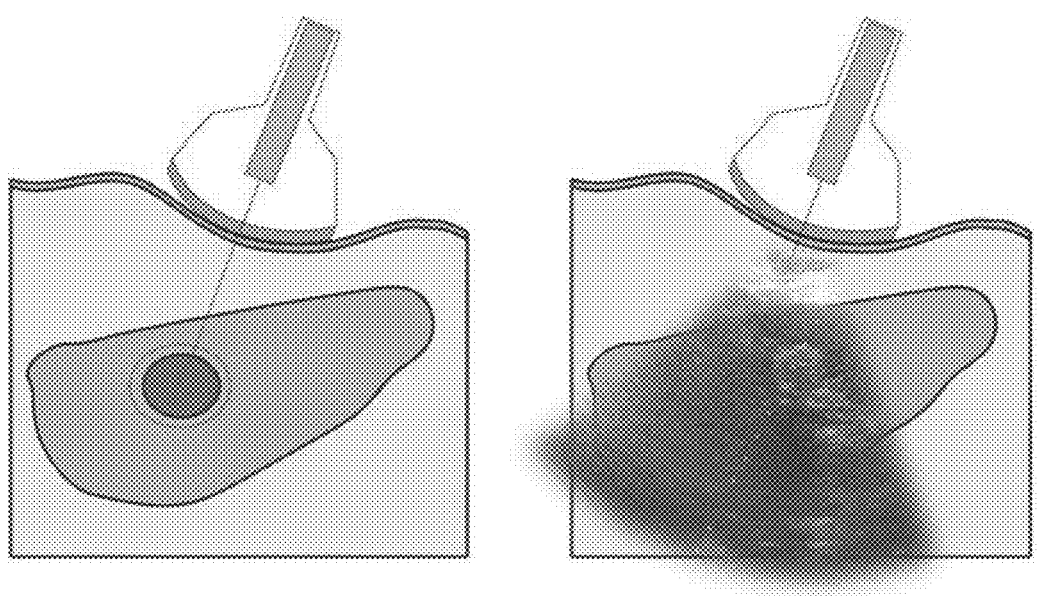
FIG. 5 shows diagrams showing an ultrasound-guided RFA treatment.

FIG. 5 shows diagrams showing an ultrasound-guided RFA treatment. In more detail, the left diagram in FIG. 5 shows the appearance of actual puncturing of RFA. The right diagram shown in FIG. 5 particularly shows the appearance of ultrasound-guided puncturing.

In a system shown in FIG. 5 to which the in vivo motion tracking device and the in vivo motion tracking method according to embodiments of the present disclosure to be described later can be applied, a doctor grips a probe and performs an RFA treatment. As shown in FIG. 5, in the ultrasound-guided RFA treatment, generally, a guide used for sticking a needle is attached to an ultrasonic probe, and an RFA needle in a shape that follows the ultrasonic probe is used for puncturing.

In a conventional tracking technique, tracking is performed by acquiring a point at which energy is minimized by using an energy function according to a plurality of templates selected in a part other than a tracking target by a doctor and an energy function according to a movement cost.

Examples of factors for a decrease in the tracking accuracy according to the conventional technique include a change in the organ, a change in the section in an ultrasonic image, and instability accompanied with manual selection of a template. Motion of an organ causes a change in the form, a change in the viewing section, rotation, and the like. According to this, a difference occurs in a viewing manner of the organ at the time of selecting a template and matching, and these are factors that decrease the accuracy of tracking through template matching.

For this reason, in the in vivo motion tracking device and the in vivo motion tracking method according to embodiments of the present disclosure to be described later, in order to solve such problems, automatic selection of a template and elimination of a deviation of a template over time through update of the template are performed.

In the in vivo motion tracking device and the in vivo motion tracking method according to embodiments of the present disclosure to be described later, in order to improve the tracking accuracy, tracking using an update-type template according to advance learning is performed. Learning data for which a correct position can be known in advance is prepared. Then, a texture analysis thereof using higher order local autocorrelation (HLAC) is performed. By using a subspace method according to a result of the analysis of a texture using the HLAC, an area similar to a texture having high tracking accuracy is detected, and automatic template selection is performed according to a result of the detection. Then, by performing the texture similarity at every fixed interval, the update-type template matching is performed.

<Characteristics of Organ Motion>

In the in vivo motion tracking device and the in vivo motion tracking method according to embodiments of the present disclosure to be described later, an in vivo motion that is a tracking target included in an ultrasonic image is, for example, a tumor of the liver. Thus, research relating to a body motion focusing on the liver is employed.

In the document by S. C. Davies, A. L. Hill, R. B. Holmes, M. Halliwell, and P. C. Jackson, "Ultrasound quantitation of respiratory organ motion in the upper abdomen," The British Journal of Radiology, 1994, S. C. Davies and coauthors measured the motion of internal organs of the upper part of the abdomen. In addition, in a document by M. A. Clifford, F. Banovac, E. Levy, and K. Cleary, "Assessment of hepatic motion secondary to respiration for computer assisted interventions," Computer Aided Surgery, 2002, M. A. Clifford and coauthors checked the motion of the liver. According to such research, it has been shown that the liver performs movement of 10 mm to 20 mm or more at a maximum speed of 15 to 20 mm/s in accordance with respiration.

In addition, in a document by D. R. Daum, N. B. Smith, et al., "In vivo demonstration of noninvasive thermal surgery of the liver and kidney using an ultrasonic phased array," Ultrasound in Med. & Biol., 1999, D. R. Daum and coauthors reported that the liver performs movement of 100 mm or more in accordance with deep respiration.

In a document by C. E. Kleynen, B. J. Slotman, F. J. Lagerwaard, J.R.v.S.d. Koste, and S. Senan, "Renal mobility during uncoached quiet respiration: an analysis of 4dct scans," International Journal of Radiation Oncology & Biology & Physics, 2006, and a document by M. Feron, B. Bussels and L. Goethal, "Respiration-induced movement of the upper abdominal organs: a pitfall for the three-dimensional conformal radiation treatment of pancreatic cancer," Radiotherapy and Oncology, 2003, there is research relating to the respiratory movement of the kidney, and it is reported that the kidney performs movement of an average of 5 to 9 mm in accordance with respiration.

In addition, in a document by D. Pham, T. Kron, F. Foroudi, M. Schneider, S. Siva, "A Review of Kidney Motion Under Free, Deep and Forced-shallow Breathing Conditions: Implications for Stereotactic Ablative Body Radiotherapy Treatment," Technology in Cancer Research & Treatment 2013, 2013, movement of 10 to 40 mm in the case of deep respiration is reported.

Accordingly, when the liver is compared with the kidney, it can be understood that the liver moves more than the kidney in accordance with respiration.

<Characteristics of Ultrasonic Image in RFA Treatment>

The in vivo motion tracking device according to the present disclosure is required to be used at the time of an actual RFA treatment. For this reason, the in vivo motion tracking device is assumed to be used at the intercostal or the intercostal. In addition, the scale is different at times, and there may be several cases in which a different part of the liver is shown. A case in which the entire contour of the liver is shown, a case in which only a part of the liver is shown, and the like may be considered. In addition, a tumor to be tracked at the time of a treatment turns white in accordance with cauterization, and it is considered not to be appropriate to perform tracking according to the tumor. Accordingly, tracking using a contour and tracking according to information of a tracking target, which are frequently used in tracking, are considered not to be appropriate for an application to the RFA treatment supporting system. Accordingly, in the in vivo motion tracking device and the in vivo motion tracking method according to embodiments of the present disclosure to be described later, tracking is performed according to the motion of an organ in an ultrasonic image rather than an in vivo motion.

Here, advantages and disadvantages directly tracking a tumor will be presented.

[Advantage]

Even when an organ changes in shape and distance relations inside the organ change, a tumor can be continuously tracked.

A tumor has a characteristic structure when compared to other tissues.

A tumor can be tracked when it is visible, and the tumor cannot be tracked when it is not visible, and thus the quality thereof is clear.

Tracking can be easily performed.

[Disadvantages]

Figure 6:
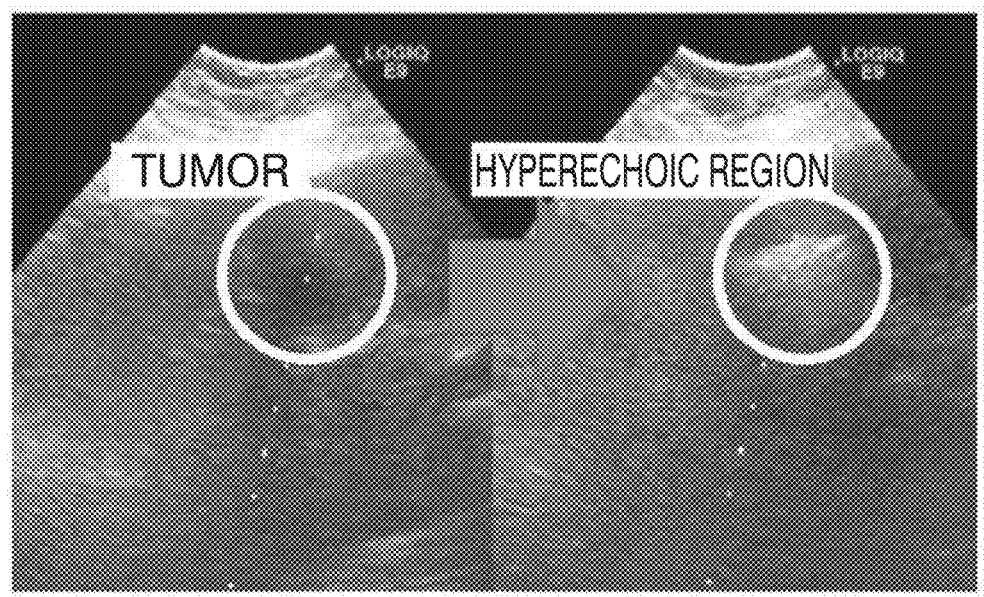
FIG. 6 is a diagram showing a hyper echoic region generated according to cauterization.

FIG. 6 is a diagram showing a hyper echoic region generated according to cauterization.

In a tumor, according to cauterization, a white area called a hyper echoic region as shown in FIG. 6 is generated. This is generated according to water vapor produced by the cauterization. The area is an area in which the external shape is greatly changed during an operation.

The area of a tumor is narrow. The tumor is greatly influenced by an acoustic shadow generated by being blocked by the intercostal.

As a tissue similar to a tumor, there is a blood vessel. When tracking is performed using only information of a narrow area, there is concern of erroneous tracking of similar tissues.

<Optimal Template in Tracking and Learning Thereof>

When the tracking of a tumor is performed, the tumor greatly changes in appearance in accordance with changes caused by the cauterization and a change in the section. According to this, it is considered to be desirable to avoid using the tumor as a template in consideration of an actual application to an operation. In view of this, the in vivo motion tracking device and the in vivo motion tracking method according to embodiments of the present disclosure to be described below, a technique is employed in which an in vivo motion peripheral portion is tracked, and the position of an in vivo motion is indirectly acquired according to a positional relation between the in vivo motion peripheral portion and an in vivo motion.

Figure 7:
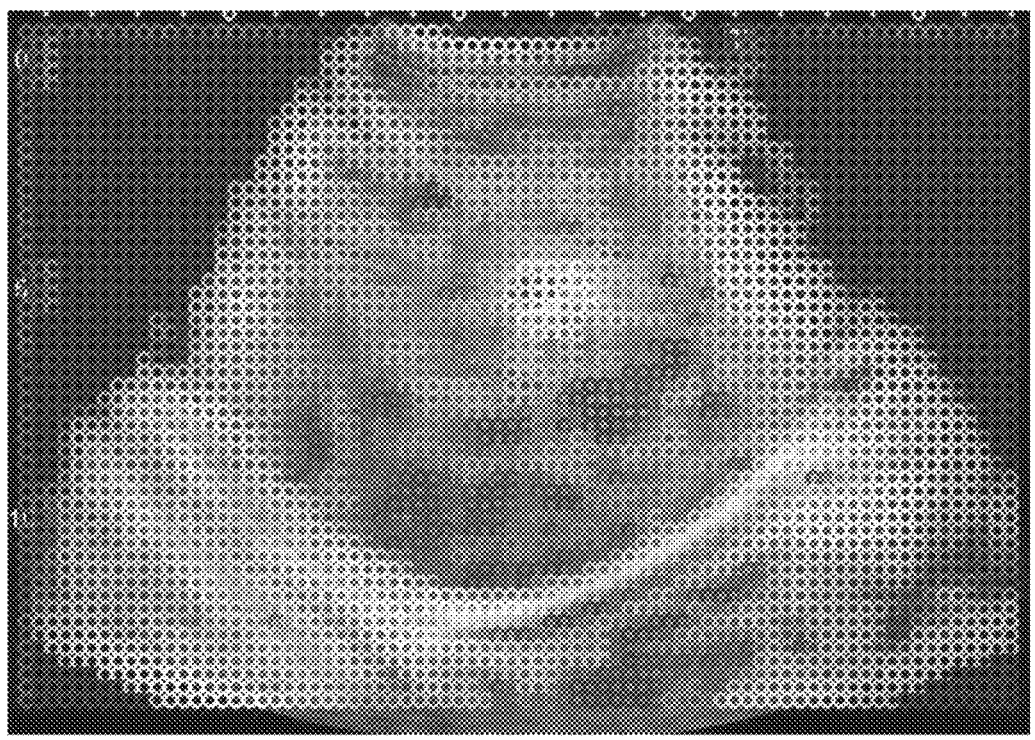
FIG. 7 is a diagram showing a result of template matching performed for each position inside an ultrasonic image using a blood vessel as a correct position.

FIG. 7 is a diagram showing a result of template matching performed for each position inside an ultrasonic image using a blood vessel as a correct position.

In FIG. 7, the height of the degree of correlation is represented using a color temperature. In FIG. 7, a white round area positioned at the center represents that the value of the degree of correlation is large. This white area represents a blood vessel part and is a tracking target. In FIG. 7, an average of the degrees of correlation according to template matching at the position of a correct point in each frame is acquired.

In FIG. 7, it can be understood that an area having a high degree of correlation, in other words, having a high tracking score, is a boundary line between the diaphragm and a shadow portion of the intercostal and another blood vessel part. Accordingly, from this, when such an area can be automatically selected, high tracking accuracy is considered to be realized. The motion of the liver is greatly influenced by the diaphragm, and it is difficult for the external shape of the diaphragm to change according to a fault offset more or less. and the diaphragm has a characteristic external shape, whereby a template including the diaphragm is considered to be appropriate for tracking. In addition, on the periphery of the acoustic shadow, particularly, only a white organ is shown due to the influence of the shadow, and it is difficult for anything else to be seen. This emphasizes a characteristic organ, and the result of tracking is considered to be improved.

In the in vivo motion tracking device and the in vivo motion tracking method according to embodiments of the present disclosure, by using a subspace method, texture information of an area having a good result of template matching using the HLAC is represented in a subspace, and the degree of similarity with the generated subspace is measured, whereby it is estimated whether an area is an appropriate area for use as a template from the texture information.

[Correct Data Acquiring Method]

In the in vivo motion tracking device and the in vivo motion tracking method according to embodiments of the present disclosure to be described later, as a correct data acquiring method, template matching is performed for the whole screen, and a portion having a good tracking result is employed as correct data that can still be a good result in the template matching. By employing this technique, a manual mapping operation of a correct position, which is generally necessary when correct data is acquired, is not necessary, and supervised learning can be automatically performed for a large amount of data.

When a template image is learned, organs of various parts are inside an ultrasonic image, and there is a difference depending on a person. Meanwhile, by applying it to the texture information to generalize information, and of a common characteristic from various kinds of learning data is achieved.

In the in vivo motion tracking device and the in vivo motion tracking method according to embodiments of the present disclosure to be described later, a part extracted as a position having high tracking accuracy is used as advance data. In a frame of which the tracking accuracy is unknown, a part similar to the characteristic of a texture at a position at which the tracking accuracy is high is selected, and the part is tracked, whereby the improvement of the tracking accuracy is targeted.

As a technique of performing tracking on the basis of texture information, in the document by Y. Ryo, "Motion Analysis of Ultrasound Image Based on Optical Flow and Texture Information," The institute of Electronics, Information and Communication Engineers Technical Research Report IMQ, Image Media Quality 113(468), 2014, Yokoyama and coauthors performed tracking with a binary characteristic amount on the periphery focused on for points of interest arranged in a lattice pattern and performed a dynamic analysis for an ultrasonic moving image in accordance with an optical flow.

Meanwhile, in the in vivo motion tracking device and the in vivo motion tracking method according to embodiments of the present disclosure to be described below, a texture is analyzed in detail, and a portion used for tracking is extracted from the whole image according to a result thereof. As a texture analyzing technique, higher order local autocorrelation (HLAC) described in a document by T. Toyoda, "Texture Classification Using Extended Higher Order Local Autocorrelation Features," Proceedings of the 4th International Workshop on Texture Analysis and Synthesis, 2005, is used. The HLAC is called a higher order local autocorrelation characteristic, and as represented in Equation (4), when an input image of a gray scale is f, is defined using an N-dimensional autocorrelation function for displacement directions $(a_1, a_2, \ldots, a_N)$.

$$x(a_1, \ldots, a_N) = \int f(r) f(r+a_1) \ldots f(r+a_N) dr \quad (4)$$

Here, the dimensions N are 0, 1, and 2.

Figure 8:
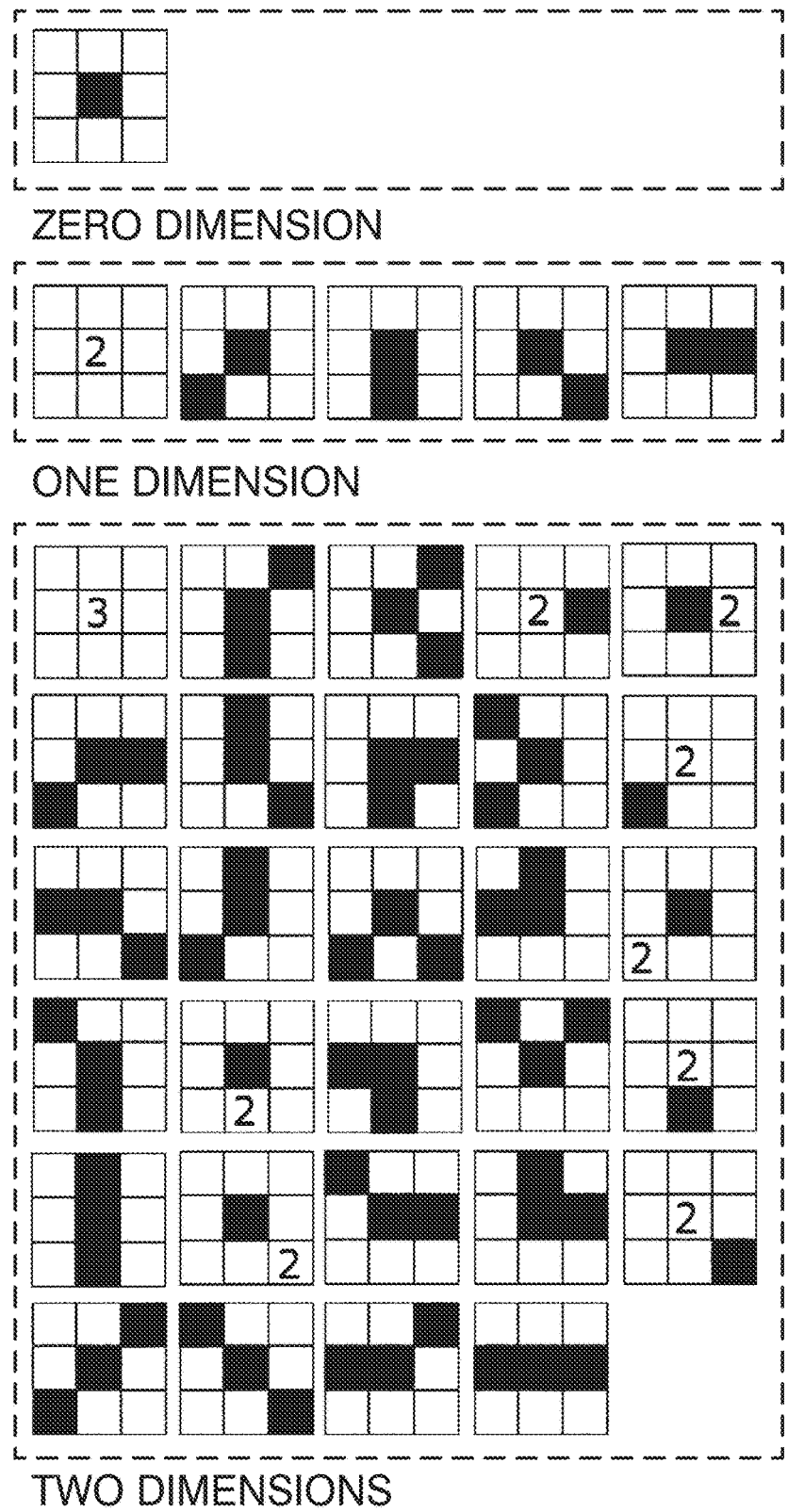
FIG. 8 is a diagram showing a high order local autocorrelation (HLAC) mask pattern.

FIG. 8 is a diagram showing an HLAC mask pattern. When r=1, the HLAC characteristic is a mask pattern as shown in FIG. 8. A black block represents the power of "1," a block in which "2" is written represents the power of "2," and a block in which "3" is written represents the power of "3." By sequentially operating for the whole range of interest in accordance with such a mask pattern, an integral characteristic is acquired. The HLAC uses the autocorrelation function, and thus is strong against noise and is also considered to exhibit an effect in a characteristic analysis of an image in which noise is included such as an ultrasonic image. There are cases in which the calculation is performed with the range of interest being 5×5 instead of 3×3 by changing the distance.

In a document by Yudai Yamazaki and Masaya Iwata, "Anomaly Detection from Breast Ultrasound Images Using AdaBoost Based on Higher-order Local Autocorrelation Feature," Research Report Mathematical Modeling and Problem Solving (MPS), Information Processing Society of Japan, 2012, as an application of the HLAC to an ultrasonic image, Yamazaki and coauthors performed a texture analysis using the HLAC in detecting a tumor part from a mammary gland ultrasonic image and performed identification of a normal mammary gland organ and a lesioned part through judgement/analysis of the acquired characteristic amount and the Adaboost. A main component analysis was performed using accumulated contribution rates of 99%, 99.9%, 99.99%, and 99.999%, characteristic spaces of 130 types were formed by combining each pattern, and identification was performed using the Adaboost for a weak identifier according thereto.

In addition, in a document by Kenji Iwata, "Toward Building Cancer Pathological Image Image Diagnosis Supporting System Using Higher-order Local Autocorrelation Feature Method (HLAC), The Japanese Society of Medical Imaging Technology Conference Proceedings, 2009, the HLAC has a characteristic of more strongly reflecting the characteristic of a high luminance part, and accordingly, two types of images including the original image and a black/white-inverted image are used.

Figure 9:
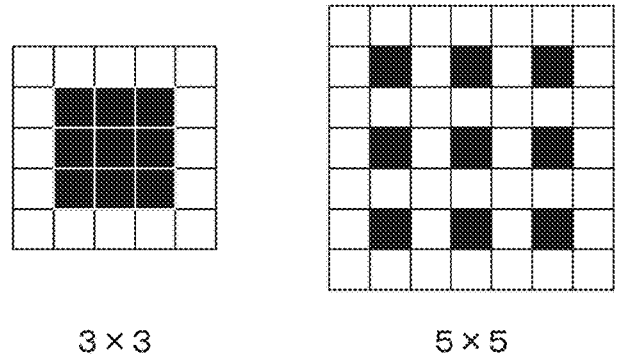
FIG. 9 is a diagram showing the size of an HLAC region of interest.

FIG. 9 is a diagram showing the size of an HLAC region of interest.

In the in vivo motion tracking device and the in vivo motion tracking method according to embodiments of the present disclosure to be described later, as shown in FIG. 9, areas of interest of 3×3 and 5×5 are set, and characteristic amounts of a total of four types of a black/white-inverted image and an un-inverted image and a total of 140 characteristic amounts are used.

<Learning According to Subspace Method>

In the subspace method, a distance of a projection component of a subspace configured by vectors, which are acquired through a learning process, into an orthogonal correction space is used. This will be set as the degree of deviation from the subspace. As the distance becomes shorter, the characteristic is similar to the characteristic at the time of learning. As the distance becomes longer, the characteristic is a characteristic different from the characteristic at the time of learning. A main component analysis is performed for the learning data, and the subspace is a space stretched by an eigenvector acquired by the main component analysis. An actual subspace method is represented by the following equation.

In the in vivo motion tracking device and the in vivo motion tracking method according to embodiments of the present disclosure to be described below, a variance-covariance matrix of an input characteristic vector $x_i$ (here, i=1 . . . N) is acquired. A main component analysis of this matrix is performed.

$$x_i (i=1 \ldots N) \quad (5)$$

$$s = \sum_{i=1}^{N} (x_i - \mu)(x_i - \mu)^T \quad (6)$$

Through the main component analysis, a subspace configured by a main component orthogonal base $U_n$ according to an eigenvector $u_k$ (here, k=0 . . . n) up to the accumulated contribution rate k is set as a subspace of a texture that is appropriate for template matching.

Next, the distance that is the degree of deviation is calculated. Here, $X_{src}$ is a vector of a texture in the input image.

At this time, the distance d can be acquired as below.

$$d^2 = X_{src}^T X_{src} - X_{src}^T U_k U_k^T X_{src} \qquad (7)$$

From this, a subspace is selected as a template that is close to a texture vector in the advance learning from a subspace having a smaller d.

<Elimination of Error Associated with Sequential Update of Template>
[Matching as Error According to Tracking Using Template Matching]

In update-type template matching, there is a problem of accumulation of errors. Generally, errors in update template matching include an error according to simple matching and an accumulated error. The accumulated error occurs due to update of a template that is performed according to a positional relation in which a prior error is present when the template is updated.

Figure 10:
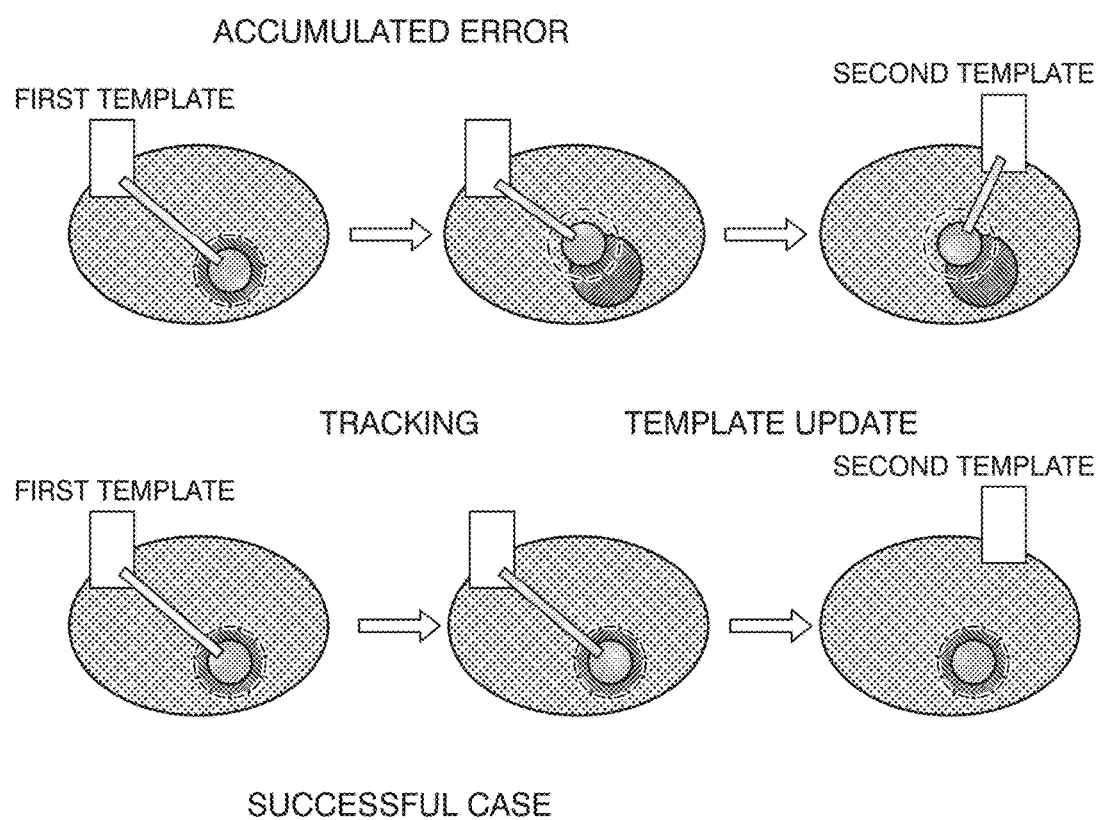
FIG. 10 shows diagrams showing a problem of the accumulation of an error in update-type template matching.

FIG. 10 shows diagrams showing a problem of the accumulation of an error in the update-type template matching.

In FIG. 10, the upper diagrams show the appearances of a case in which a template is updated in a state in which there is an error according to template matching. When compared with a case in which update is performed in a state in which there is no error shown in the lower diagrams, it can be understood that a reference position deviates at the moment when update is performed. In this way, in the update-type template matching, there is a problem of drift in which the tracking position slightly deviates each time in accordance with the accumulation of the error.

Figure 11:
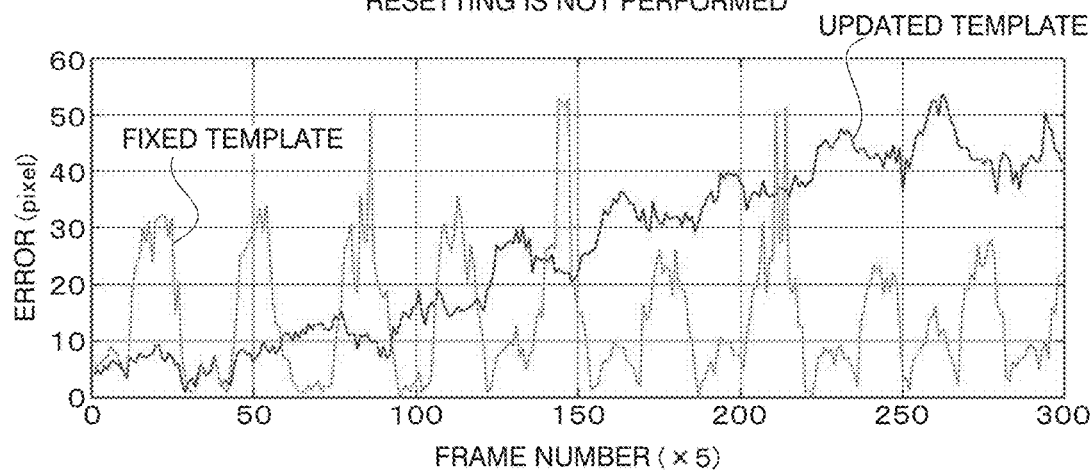
FIG. 11 is a diagram showing a case in which a problem of drift occurs in actual tracking of an ultrasonic moving image (an error of a case in which resetting is not performed)

FIG. 11 is a diagram showing a case in which a problem of drift occurs in actual tracking of an ultrasonic moving image (an error of a case in which resetting is not performed).

Figure 12:
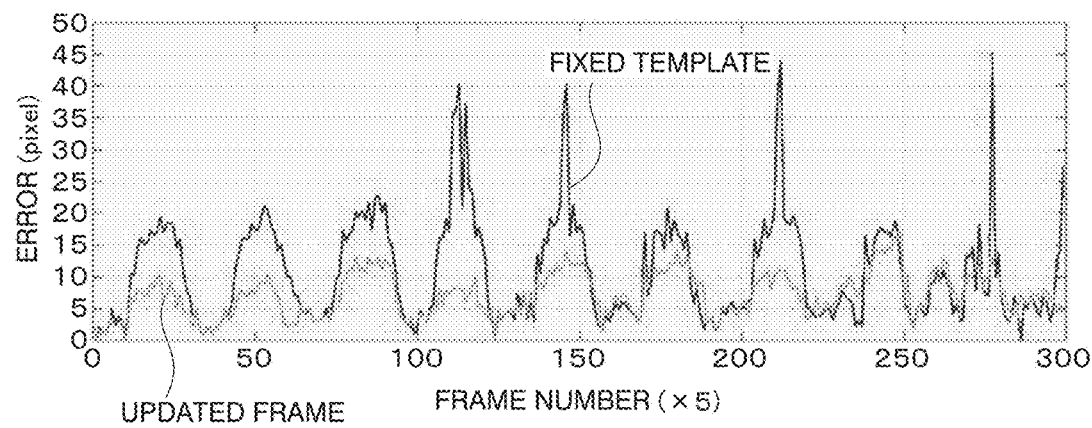
FIG. 12 is a diagram showing errors from correct coordinates in an actual ultrasonic moving image in a case in which a template is not updated and a case in which a template is updated.

FIG. 12 is a diagram showing errors from correct coordinates in an actual ultrasonic moving image in a case in which a template is not updated and a case in which a template is updated.

In the update-type template matching, compared with a case in which update is not performed, while an initial error is small, the appearance in which the error is accumulated in accordance with the elapse of time and the error increases is shown. Accordingly, when compared with a case in which update is not performed, it can be understood that an error is large in the update-type template matching in a later stage.

Hereinafter, an in vivo motion tracking device and an in vivo motion tracking method according to embodiments of the present disclosure will be described with reference to the drawings.

<First Embodiment>

Figure 13:
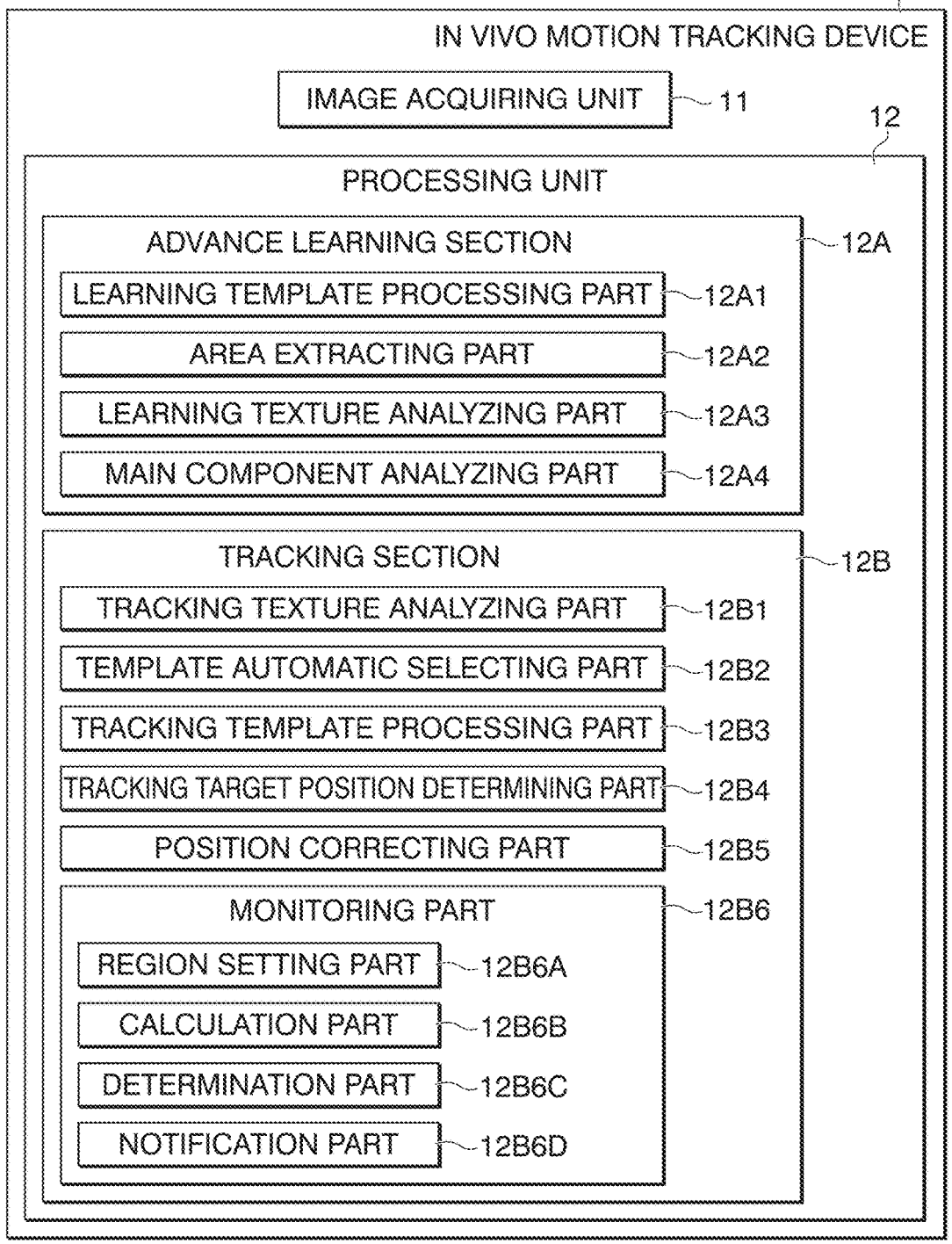
FIG. 13 is a diagram showing an example of the configuration of an in vivo motion tracking device according to a first embodiment.

FIG. 13 is a diagram showing an example of the configuration of an in vivo motion tracking device 1 according to a first embodiment. The in vivo motion tracking device 1 according to the first embodiment tracks an in vivo motion that is a tracking target included in an ultrasonic image.

In more detail, the in vivo motion tracking device 1 tracks a focused portion operating in connection with an organ approximately periodically performing a motion inside a living body in a living body image acquired by imaging a living body structure. Here, organs of interest as observation targets or tracking targets are, for example, the liver and the kidney. The kidney and the liver approximately periodically move in accordance with respiration of a living body such as a patient. The focused portion is typically a lesioned part and, for example, is a stone, cancer, a tumor, or the like.

The in vivo motion tracking device 1 is, for example, used for supporting ultrasound-guided RFA treatment. In another example, the in vivo motion tracking device 1 may be, for example, used for supporting a high intensity focused ultrasound (HIFU) treatment.

In the example shown in FIG. 13, the in vivo motion tracking device 1 includes an image acquiring unit 11 and a processing unit 12. The image acquiring unit 11, for example, acquires an ultrasonic image captured using a probe or the like. The processing unit 12 includes an advance learning section 12A and a tracking section 12B. The advance learning section 12A performs advance learning, for example, using ultrasonic images prepared in advance as learning data. After the advance learning performed using the advance learning section 12A, the tracking section 12B tracks a position of a tracking target in an ultrasonic image including the tracking target.

In the example shown in FIG. 13, the advance learning section 12A includes a learning template processing part 12A1, an area extracting part 12A2, a learning texture analyzing part 12A3, and a main component analyzing part 12A4.

The learning template processing part 12A1 performs a template process using an ultrasonic image of the learning data. In more detail, the learning template processing part 12A1 performs the template matching described with reference to FIG. 3 using an ultrasonic image of the learning data.

The area extracting part 12A2 extracts an area included in the ultrasonic image of the learning data. The learning texture analyzing part 12A3 performs a texture analysis for the area extracted by the area extracting part 12A2. The main component analyzing part 12A4 performs a main component analysis for a result of the texture analysis performed by the learning texture analyzing part 12A3.

In the example shown in FIG. 13, the tracking section 12B includes a tracking texture analyzing part 12B1, a template automatic selecting part 12B2, a tracking template processing part 12B3, a tracking target position determining part 12B4, a position correcting part 12B5, and a monitoring part 12B6.

The tracking texture analyzing part 12B1 performs a texture analysis of an ultrasonic image including a tracking target. The template automatic selecting part 12B2 selects an image area that is appropriate for tracking the tracking target as a template on the basis of a result of the texture analysis performed by the tracking texture analyzing part 12B1 and a result of the learning performed by the advance learning section 12A.

The tracking template processing part 12B3 performs an update-type template process for each of a plurality of templates that are sequentially selected by the template automatic selecting part 12B2. In more detail, the tracking template processing part 12B3 performs update-type template matching.

The tracking target position determining part 12B4 determines a position having a highest degree of correlation as a position of the tracking target on the basis of a result of the template process for a plurality of templates performed by the tracking template processing part 12B3.

The position correcting part 12B5 performs position correction according to an initial template having no accumulated error. In more detail, when matching using the initial template has a degree of correlation having a predetermined value or more, the position correcting part 12B5 corrects the position of the tracking target to the position of the tracking target at that time point.

The monitoring part 12B6 constantly monitors a region of interest (ROI). The monitoring part 12B6 includes a region setting part 12B6A, a calculation part 12B6B, a determination part 12B6C, and a notification part 12B6D. The region setting part 12B6A sets a template of the initial region of interest. After tracking, the calculation part 12B6B calculates a distance between the template of the initial region of interest set by the region setting part 12B6A and a region of interest that is currently tracked. The determination part 12B6C determines whether or not the distance calculated by the calculation part 12B6B exceeds a predetermined threshold. The notification part 12B6D performs notification with an alarm when the distance calculated by the calculation part 12B6B exceeds the predetermined threshold. When the distance calculated by the calculation part 12B6B exceeds the predetermined threshold, the notification part 12B6D, together with performing notification through the alarm, may store an image of a corresponding region of interest in a database (not shown in the drawing) in a readable form. This database may be either local or on a network.

Figure 14:
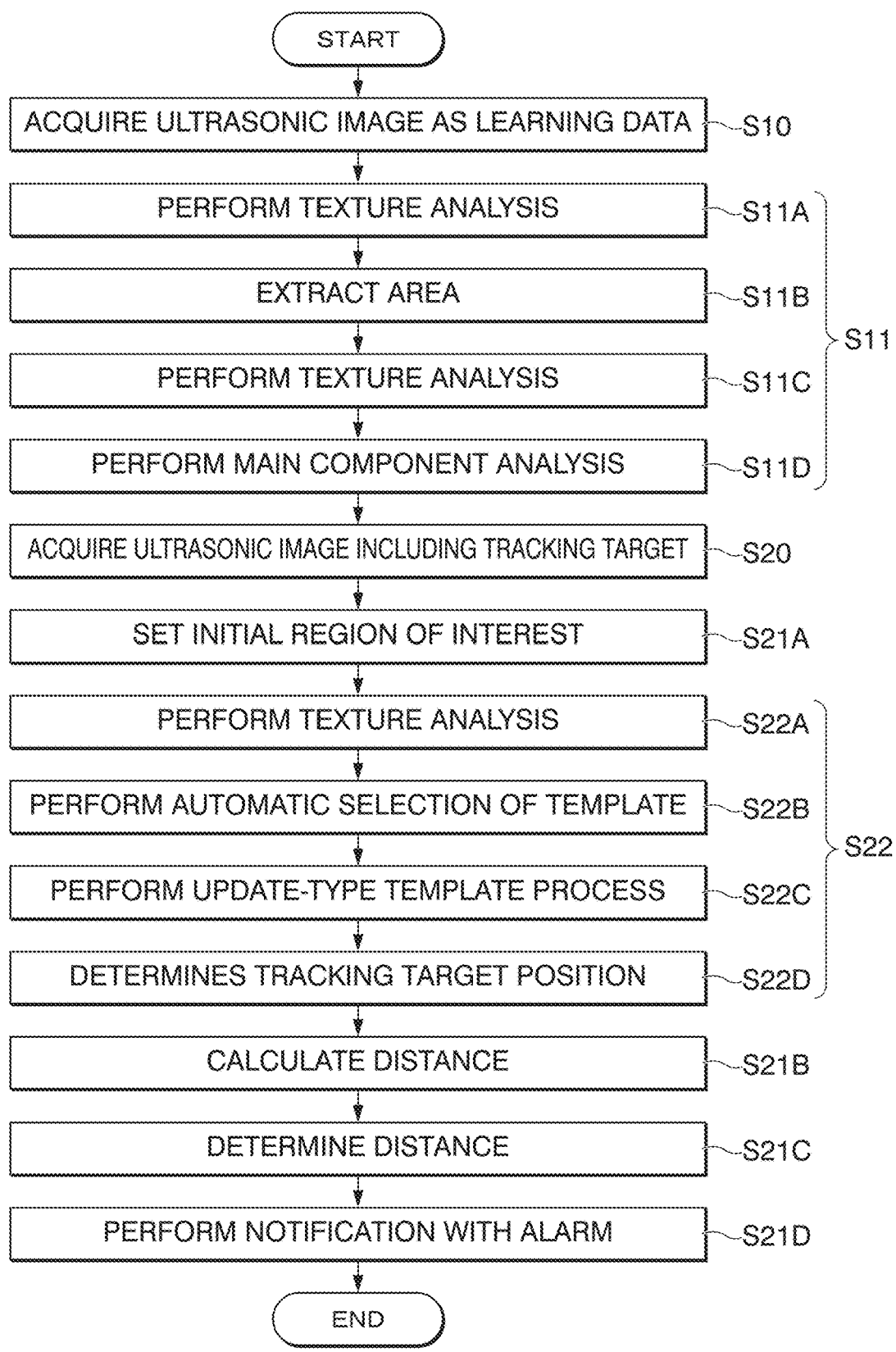
FIG. 14 is a flowchart schematically showing the flow of a process performed by the in vivo motion tracking device according to the first embodiment.

FIG. 14 is a flowchart schematically showing the flow of a process performed by the in vivo motion tracking device 1 according to the first embodiment.

In the example shown in FIG. 14, in Step S10, the image acquiring unit 11 acquires an ultrasonic image as learning data.

Next, in Step S11, the advance learning section 12A performs advance learning using the ultrasonic image as learning data. Step S11 includes Step S11A, Step S11B, Step S11C, and Step S11D.

First, in Step S11A, the learning template processing part 12A1 performs a template process using the ultrasonic image of the learning data.

Next, in Step S11B, the area extracting part 12A2 extracts a region included in the ultrasonic image of the learning data.

Next, in Step S11C, the learning texture analyzing part 12A3 performs a texture analysis of the region extracted in Step S11B.

Next, in Step S11D, the main component analyzing part 12A4 performs a main component analysis of a result of the texture analysis performed in Step S11C.

Steps S11A to S11D are processes performed by the advance learning section 12A.

Next, in Step S20, the image acquiring unit 11 acquires an ultrasonic image including the tracking target.

Next, in Step S21A, the region setting part 12B6A sets the template of the initial region of interest. In the example shown in FIG. 14, the region setting part 12B6A performs automatic setting using a plurality of templates that are automatically extracted by the region setting part 12B6A. This is because a template appropriate for tracking that is automatically selected is a template in which a texture of a living body structure appears relatively clearly, and thus is considered to be a template of a region that is also similarly appropriate for detecting a change (abnormality) from the initial template. In another example, the region setting part 12B6A may extract and set a template of the initial region of interest from a past diagnosis image database of the same person. In another example, a doctor may set a template of the initial region of interest.

Next, in Step S22, the tracking section 12B tracks the position of the tracking target in the ultrasonic image including the tracking target. Step S22 includes Step S22A, Step S22B, Step S22C, and Step S22D.

First, in Step S22A, the tracking texture analyzing part 12B1 performs a texture analysis of the ultrasonic image including the tracking target.

Next, in Step S22B, the template automatic selecting part 12B2 selects an image area that is appropriate for tracking the tracking target on the basis of a result of the texture analysis in Step S22A and a result of the learning in Step S11.

Next, in Step S22C, the tracking template processing part 12B3 performs an update-type template process for each of the plurality of templates sequentially selected in Step S22B.

Next, in Step S22D, the tracking target position determining part 12B4 determines a position having a highest degree of correlation as the position of a tracking target on the basis of a result of the template process for the plurality of templates in Step S22C.

In addition, in Step S22, as necessary, the position correcting part 12B5 performs a position correction according to the initial template having no accumulated error.

Next, in Step S21B, the calculation part 12B6B, after tracking, calculates a distance between the template of the initial region of interest set by the region setting part 12B6A and a region of interest that is currently tracked.

Next, in Step S21C, the determination part 12B6C determines whether or not the distance calculated by the calculation part 12B6B exceeds the predetermined threshold.

Next, in Step S21D, the notification part 12B6D performs notification with an alarm when the distance calculated by the calculation part 12B6B exceeds the predetermined threshold.

Step S21A to Step S21D are processes performed by the tracking section 12B.

As described above, in the example shown in FIGS. 13 and 14, the learning template processing part 12A1 performs a template process using an ultrasonic image of the learning data, and the tracking template processing part 12B3 performs an update-type template process for each of a plurality of templates that are sequentially selected by the template automatic selecting part 12B2.

In another example, instead of this, one template processing unit may perform a template process using an ultrasonic image of the learning data and perform an update-type template process for each of the plurality of templates that are sequentially selected by the template automatic selecting part 12B2.

The distance in Step S21B is a distance (difference) of the image characteristic amounts between the template of the initial region of interest in the template matching and a region of interest that is currently tracked. Individually, the distance is largely divided into the following four.

(1) Mutual correlation coefficient between the template of the initial region of interest in the template matching and the region of interest that is currently tracked The distance is, for example, a sum of squared differences (SSD). As the SSD, raster scanning of the template is performed, and a sum of squares of differences between the luminance values of a pixel located at the same position is used. As the value of the SSD decreases, the positions become more similar to each other.

In addition, the distance, for example, is a sum of absolute differences (SAD). As the SAD, raster scanning of the template is performed, and a sum of absolute values of differences between the luminance values of a pixel located at the same position is used. As the value of the SAD decreases, the positions become more similar to each other.

In addition, the distance is, for example, a normalized cross-correlation (NDD). As the degree of similarity between the template and the image, there are cases in which the normalized cross-correlation is used. As the degree of similarity is closer to "1," the positions are more similar to each other.

(2) Difference of texture characteristic amounts between the template of the initial region of interest in the template matching and the region of interest that is currently tracked The HLAC described above is included in this.

More specifically, the distance is, for example, a texture characteristic amount using a Hough transformation.

In addition, the distance is, for example, a texture characteristic amount using a density histogram.

Furthermore, the distance is, for example, a texture characteristic amount using a Fourier spectrum.

In addition, the distance is, for example, a texture characteristic amount using a difference statistic.

Furthermore, the distance is, for example, a texture characteristic amount using a gray level co-occurrence matrix.

In addition, the distance is, for example, a texture characteristic amount using a run length matrix.

Furthermore, the distance is, for example, a texture characteristic amount using a fractal.

(3) Difference between the template of the initial region of interest in the template matching and the (contour) shape (flatness, curvature, contour length, diameter, or area) of an organ inside the region of interest that is currently tracked (4) Image characteristic amount described on the eleventh page of the following document http://www.vision.c-s.chubu.ac.jp/features/PPT/SSII2009/090610_SSII2009_Tutorial.pdf Relating to the distance (difference) of the image characteristic amounts between the template of the initial region of interest in the template matching and the region of interest that is currently tracked, the template image may have a different dimension (for example, the template has three dimensions, and the region of interest is two dimensions). The image diagnosis modalities (CT or MRI) thereof may be different from each other. A shaped (already not an image) characteristic amount taken from a database may be used.

As described above, in the example shown in FIGS. 13 and 14, the learning texture analyzing part 12A3 performs a texture analysis of a region extracted by the region extracting part 12A2, and the tracking texture analyzing part 12B1 performs a texture analysis of an ultrasonic image including the tracking target.

In another example, instead of this, one texture analyzing part may perform a texture analysis of a region extracted by the area extracting part 12A2 and perform a texture analysis of an ultrasonic image including the tracking target.

As described above, a tracking technique used by the in vivo motion tracking device 1 according to the first embodiment is configured by two processes including advance learning and actual tracking.

In the advance learning, template matching is performed using learning data, and a region having a good result is extracted. For this, a texture analysis is performed. Accordingly, a texture characteristic that is appropriate for template matching is acquired. By performing a main component analysis of this, data of a learning result is acquired.

In actual tracking, a texture analysis is performed for an input image. According to this result and the data of the learning result, whether or not the texture is appropriate for template matching is represented as the degree of similarity using the subspace method. Among them, regions having high degrees of similarity are selected as templates, whereby automatic selection is performed. In addition, selection of a template is sequentially performed, and tracking is performed using update-type template matching of performing tracking while changing the template. In addition, matching is performed for each of a plurality of templates. Then, after such results are added together as represented in the following equation, coordinates having a highest degree of correlation are set as a position of a tracking target.

$$sumR_t = \frac{1}{N} \sum_{k=1}^{n} \sum_{u_{tk_0}}^{u_{tk_1}} \sum_{v_{tk_0}}^{v_{tk_1}} R_{u,v} \quad (8)$$

In addition, in actual tracking, there is a problem in that an accumulated error occurs in the update-type template matching, and thus, in order to prevent such a problem, the position is corrected. The correction of the position is performed according to the initial template in which there is no accumulated error. When the matching using the initial template has a degree of correlation of a fixed value or more, the positional relation at that time has high reliability, and the position is corrected to the position of the in vivo motion position at that time. The update-type template matching in which these processes are sequentially performed is used for actual tracking.

Figure 15:
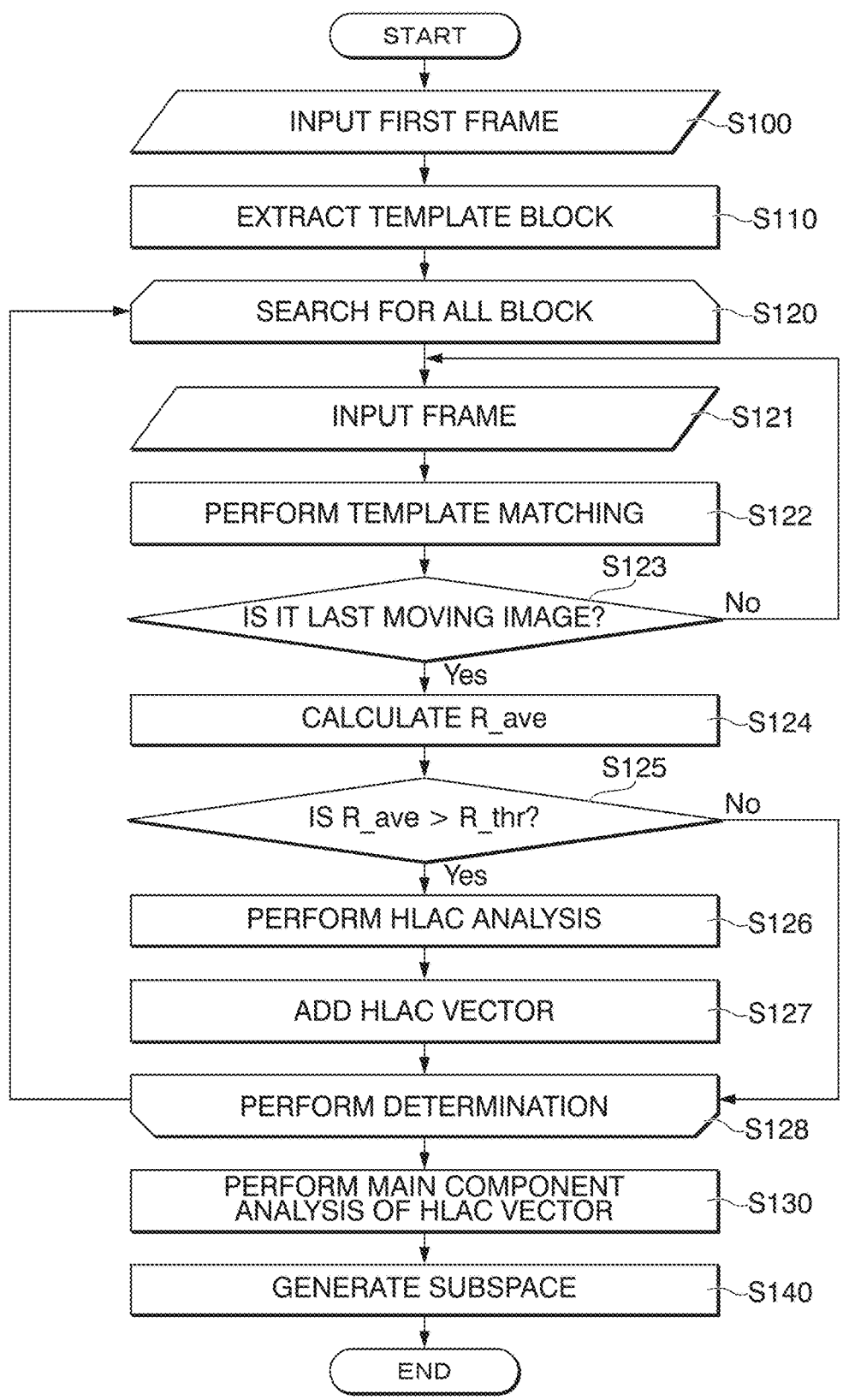
FIG. 15 is a flowchart showing a specific example for realizing Step S11 shown in FIG. 14.

FIG. 15 is a flowchart showing a specific example for realizing Step S11 shown in FIG. 14.

In the example shown in FIG. 15, in Step S100, a first frame is input. The first frame, for example, configures a part of an ultrasound moving image for advance learning and is, for example, an ultrasound still image at time t1.

Next, in Step S110, all the template blocks included in the first frame are extracted. The template blocks are, for example, blocks acquired by dividing the first frame into a plurality of rectangular partitions.

Next, in Step S120, all the blocks are retrieved. More specifically, in Step S121, a frame is input. Next, in Step S122, template matching is performed. Next, in Step S123, it is determined whether or not it is the end of the moving image. When it is the end of the moving image, the process proceeds to Step S124. On the other hand, when it is not the end of the moving image, the process is returned to Step S121.

In Step S124, the average correlation coefficient R_ave is calculated. Next, in Step S125, it is determined whether or not the average correlation coefficient R_ave is larger than a threshold R_thr. When the average correlation coefficient R_ave is larger than the threshold R_thr, the process proceeds to Step S126. On other hand, when the average correlation coefficient R_ave is the threshold R_thr or less, the process proceeds to Step S128.

In Step S126, an HLAC analysis is performed. Next, in Step 127, addition of HLAC vectors is performed, and then the process proceeds to Step S128.

In Step S128, it is determined whether or not the retrieval of all the blocks has been completed. When the retrieval of all the blocks has been completed, the process proceeds to Step S130. On the other hand, when the retrieval of all the blocks has not been completed, the process is returned to Step S120.

In Step S130, a main component analysis of an HLAC vector is performed.

Next, in Step S140, a subspace is generated.

Figure 16:
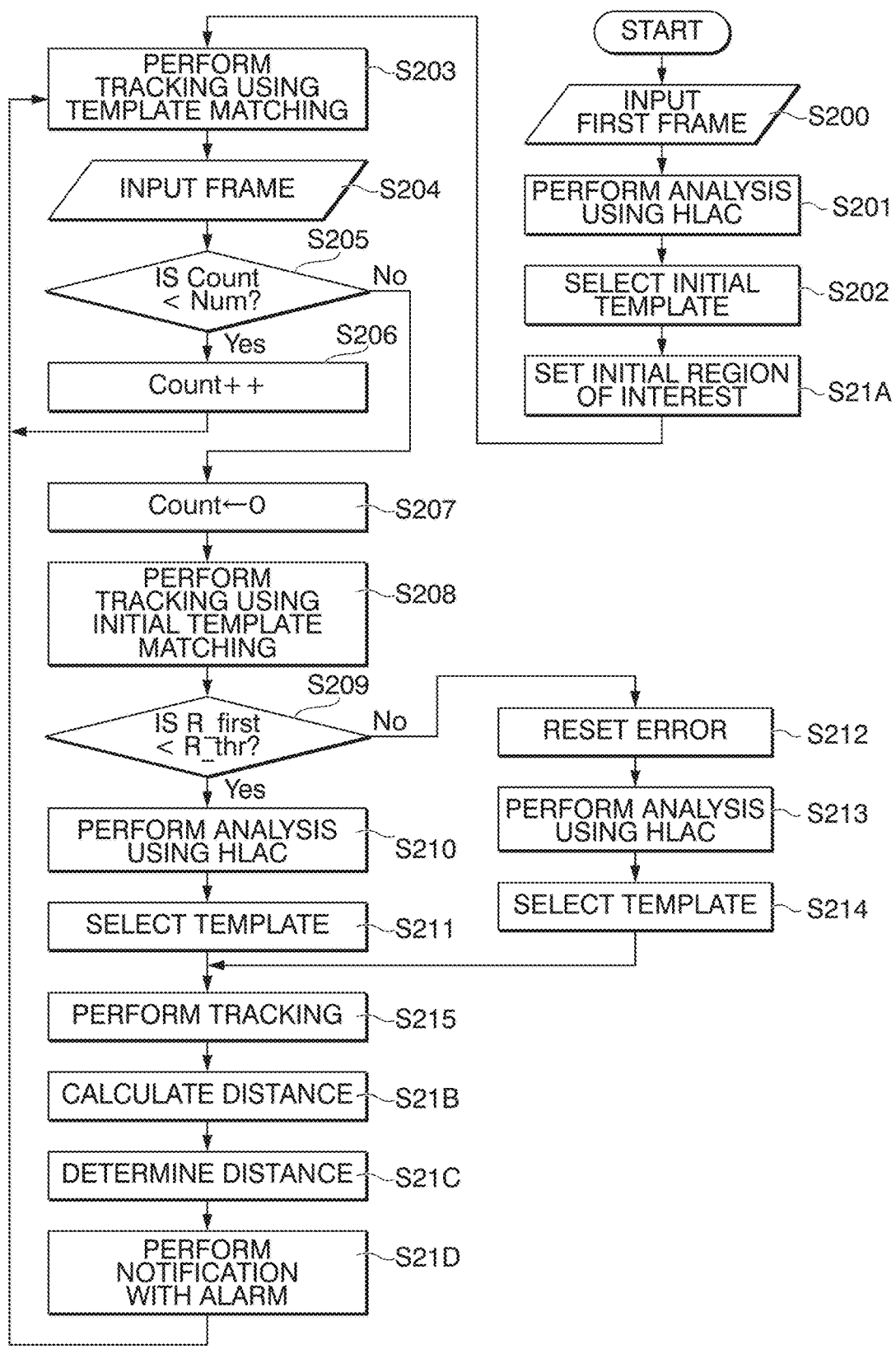
FIG. 16 is a flowchart showing a specific example for realizing Step S22 and the like shown in FIG. 14.

FIG. 16 is a flowchart showing a specific example realizing Step S22 and the like shown in FIG. 14.

In the example shown in FIG. 16, in Step S200, a first frame is input. The first frame, for example, configures a part of an ultrasonic moving image for tracking, and for example, is an ultrasonic still image at time t01.

Next, in Step S201, an analysis using the HLAC is performed.

Next, in Step S202, an initial template is selected using a subspace method.

Next, in Step S21A, the region setting part 12B6A sets a template of the initial region of interest.

Next, in Step S203, tracking using template matching is performed.

Next, in Step S204, a frame is input.

Next, in Step S205, it is determined whether or not a counter value Count is smaller than a predetermined value Num. When the counter value Count is smaller than the predetermined value Num, the process proceeds to Step S206. On the other hand, when the counter value Count is the predetermined value Num or more, the process proceeds to Step S207.

In Step S206, the counter value Count is incremented, and the process is returned to Step S203.

In Step S207, the counter value Count becomes zero, and the process proceeds to Step S208.

In Step S208, tracking using the initial template matching is performed.

Next, in Step S209, it is determined whether or not the initial correlation coefficient R_first is smaller than the threshold R_thr. When the initial correlation coefficient R_first is smaller than the threshold R_thr (in other words, the accumulated error is small), the process proceeds to Step S210. On the other hand, when the initial correlation coefficient R_first is the threshold R_thr or more (in other words, the accumulated error is large), the process proceeds to Step S212.

In Step S210, an analysis using the HLAC is performed.

Next, in Step S211, a template is selected using the subspace method, and the process proceeds to Step S215.

In Step S212, the error is reset using a result of the initial template matching.

Thereafter, in Step S213, an analysis using the HLAC is performed.

Next, in Step S214, a template is selected using the subspace method, and the process proceeds to Step S215.

In Step S215, a position of the tracking target is determined, and tracking is performed.

Next, in Step S21B, the calculation part 12B6B, after the tracking, calculates a distance between the template of the initial region of interest and the region of interest that is currently tracked.

Next, in Step S21C, the determination part 12B6C determines whether or not the distance calculated by the calculation part 12B6B exceeds a predetermined threshold.

Next, in Step S21D, the notification part 12B6D performs notification with an alarm when the distance calculated by the calculation part 12B6B exceeds the predetermined threshold and does not perform notification with an alarm when the distance calculated by the calculation part 12B6B is the predetermined threshold or less. Next, the process is returned to Step S202.

Figure 17:
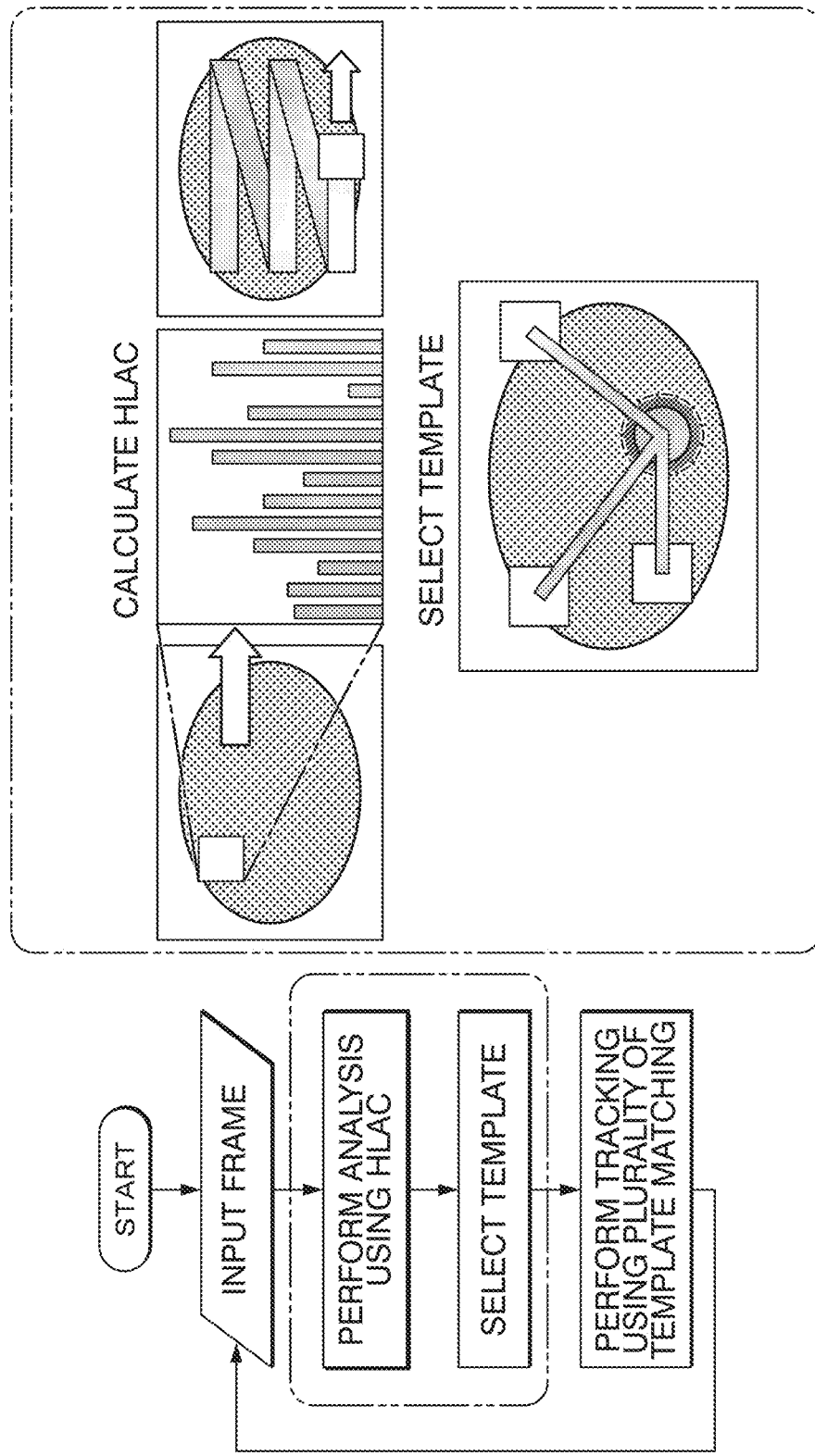
FIG. 17 is a diagram showing a relation between an analysis using the HLAC (Steps S201, S210, and S213) and selection of a template using a subspace method (Steps S202, S211, and S214) in the case shown in FIG. 16.

FIG. 17 is a diagram showing a relation between an analysis using the HLAC (Steps S201, S210, and S213) and selection of a template using the subspace method (Steps S202, S211, and S214) in the case shown in FIG. 16.

As shown in FIG. 17, the tracking section 12B selects regions having texture characteristic amounts having high degrees of similarity with the texture characteristic amount using the HLAC acquired by the advance learning using the subspace method as a plurality of templates. In addition, the tracking section 12B collates matching results for the templates according to this as in Equation 7. Furthermore, the tracking section 12B acquires coordinates at which the value of $sumR_t$ represented in Equation 8 is maximum. In Equation 8, N represents the number of templates, and $R_{u, v}$ represents the degree of correlation at each of coordinates. The tracking section 12B performs tracking with the acquired coordinates regarded as an in vivo motion in the frame.

Figure 18:
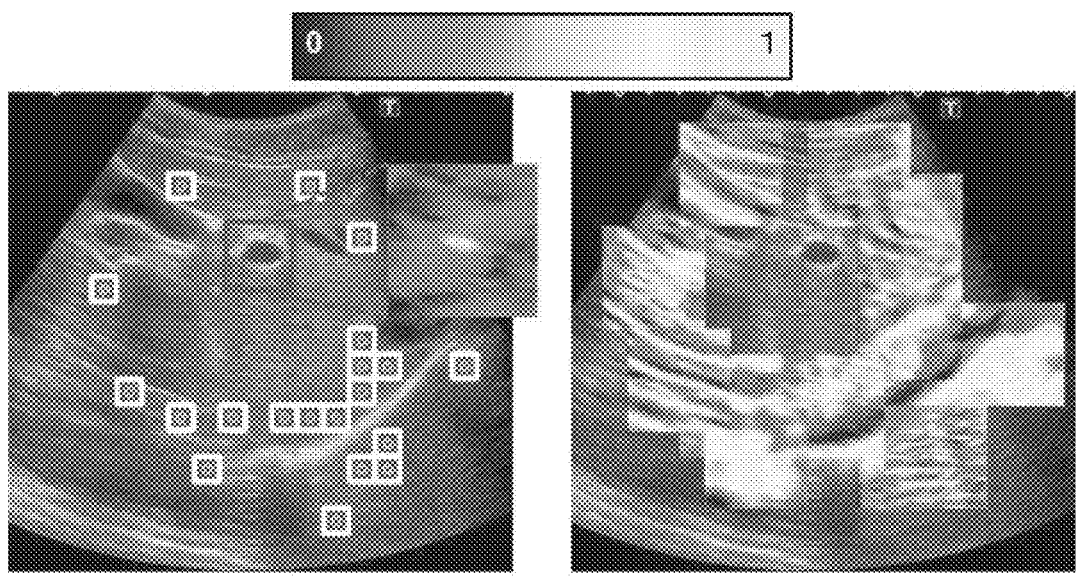
FIG. 18 shows diagrams showing tracking of a tracking target using template matching and a correlation coefficient of each template.

FIG. 18 shows diagrams showing tracking of a tracking target using template matching and a correlation coefficient of each template. In FIG. 18, each portion enclosed by a square of white lines represents a template. In the right diagram of FIG. 18, for example, large white areas inside portions enclosed by squares positioned at the right end and the lower left side represent regions having large correlation coefficients (the degrees of correlation are high).

<Second Embodiment>

As described above, in the in vivo motion tracking device 1 according to the first embodiment, the learning template processing part 12A1 uses an ultrasonic image of learning data, thereby performing template matching.

On the other hand, in an in vivo motion tracking device 1 according to a second embodiment, a learning template processing part 12A1 performs kernelized correlation filters (KCF) tracking using an ultrasonic image of learning data. In more details, the learning template processing part 12A1 performs the KCF tracking using a technology described in a document "Henriques, J., Caseiro, R., Martins, P., & Batista, J. High-Speed Tracking with Kernelized Correlation Filters. IEEE Transactions on Pattern Analysis and Machine Intelligence (TPAMI) 37(3), 583-596".

In addition, as described above, in the in vivo motion tracking device 1 according to the first embodiment, the tracking template processing part 12B3 performs the update-type template matching.

On the other hand, in the in vivo motion tracking device 1 according to the second embodiment, a tracking template processing part 12B3 performs KCF tracking.

<Monitoring Technique>

In a system to which the in vivo motion tracking device 1 according to the first or second embodiment is applied, in addition, to treatment support for a doctor through superimposing display of a real tumor position on a tumor that is in the middle of cauterization, a tumor cauterization status can be monitored through an observation of luminance information of an image in the range of the tumor that is tracked.

As a method of evaluating the cauterization status used by a doctor, currently, a visual evaluation using an ultrasonic moving image, a visual evaluation using a contrast medium, an evaluation after an operation using CT or MR, or the like is performed. In a system to which the in vivo motion tracking device 1 according to the first or second embodiment is applied, as a technique for monitoring the cauterization status in real time, a quantitative display of the cauterization status is performed for supporting a visual evaluation of an ultrasonic moving image.

When the cauterization is performed, the periphery of a tumor changes to be white. This is called a hyper echoic region and is caused by water vapor generated by the heat of the cauterization. A doctor performs a determination of the current cauterization status and the like in a state in which the region changed to be white is enlarged or the like.

In a system to which the in vivo motion tracking device 1 according to the first or second embodiment is applied, the average luminance of a tumor part and a change in the average luminance of the cauterization margin in time are measured on the basis of the current position of the tumor acquired through tracking, and the cauterization status is quantitatively presented through display of the amount of change in real time.

In this monitoring technique, the appearance of a change in the luminance of a tumor is observed from the initial period, and thus, it is important to correctly track the position of the tumor. From this, from two viewpoints including the presentation of the position of the in vivo motion through superimposed display and the monitoring of the luminance value of the in vivo motion, tracking of an in vivo motion having high accuracy is required.

<Application Example>

Figure 19:
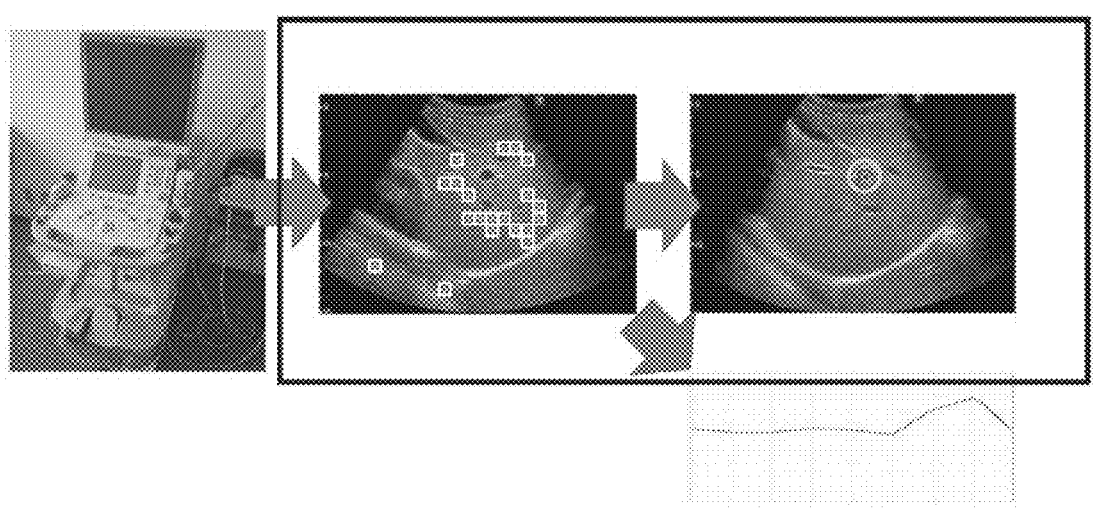
FIG. 19 is a diagram showing an example of a system to which the in vivo motion tracking device according to the first or second embodiment is applied.

FIG. 19 is a diagram showing an example of a system to which the in vivo motion tracking device 1 according to the first or second embodiment is applied.

In the example shown in FIG. 19, an ultrasonic image is input to the system, tracking described with reference to FIG. 16 is performed, and display of a result of the tracking and monitoring are performed.

<Tracking Experiment in Normal Liver of Case where Update Frame is Changed>

In update-type template matching, the update timing of a frame relates much to the tracking accuracy. Thus, the inventors of the present disclosure and others measured tracking accuracy at a plurality of update timings for an ultrasonic moving image of the same normal liver and performed an experiment for acquiring the influence of the update timing on the tracking accuracy in template matching and an optimal update timing.

For one type of ultrasonic moving image of a normal liver, the update timing is set at frame numbers 2 to 10. When this is presented in sections in this moving image having an fps of 18, it corresponds to 0.11 seconds to 0.83 seconds. Then, the average tracking error and the standard deviation of each frame are acquired, and they are compared with each other.

Figure 20:
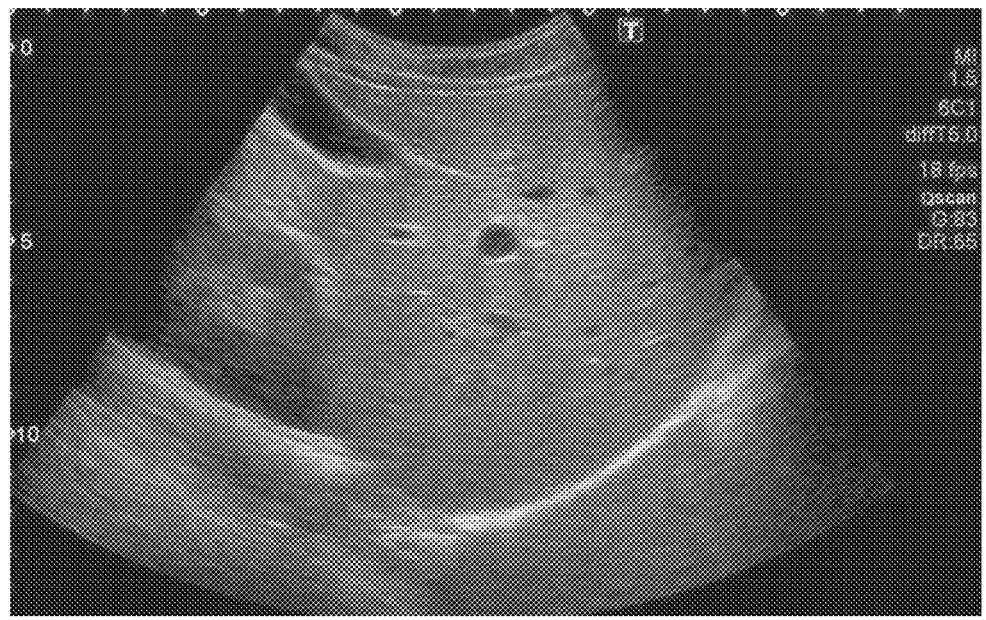
FIG. 20 shows one frame of a moving image used in a tracking experiment.

FIG. 20 shows one frame of a moving image used in the tracking experiment. The moving image used in the tracking experiment was captured from the intercostal.

[Moving Image for Learning]

In this experiment, as moving images for learning, four types of moving images of a normal liver were acquired at the interval of 20 frames, and the tracking accuracy during 200 frames was measured for each frame. From this, learning was performed on the basis of a total of 97 images.

Figure 21:
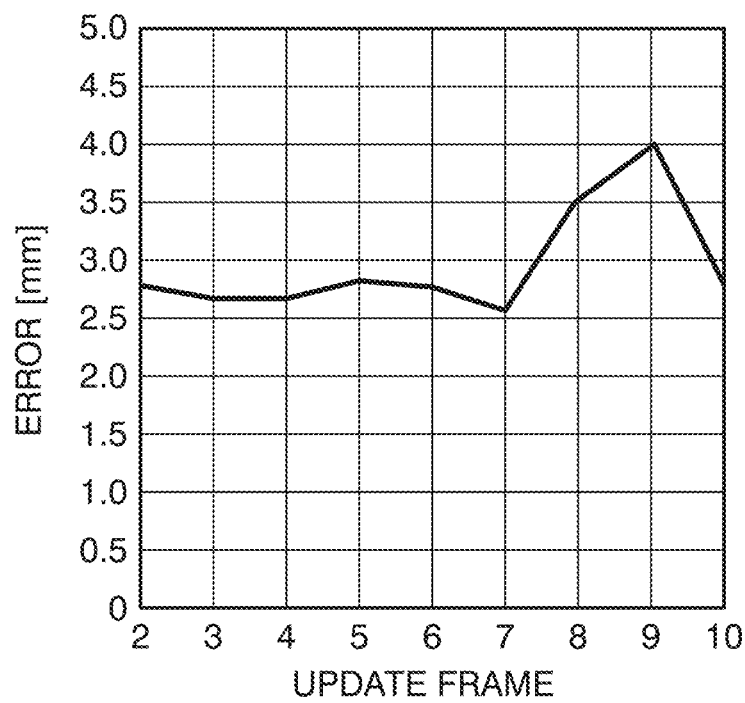
FIG. 21 is a diagram showing an error [mm] at each update timing.

FIG. 21 is a diagram showing an error [mm] at each update timing.

As shown in FIG. 21, it can be understood that, at the update frame numbers 2, 3, 4, and 7, the average tracking error is lowered, and the tracking accuracy is high. In other words, when the update frame number is small, the tracking accuracy tends to be high. Several reasons for this may be considered.

1. A change in the form of an organ or a change in the section accompanying respiration occurs in accordance with the elapse of time. Accordingly, a difference between the template and the ultrasound moving image at the time of matching occurs. This is a problem of lowering the accuracy of the template matching. When the difference between the template and the ultrasonic image increases, a region that is a candidate for a template may broadly present on the periphery of the correct position or a candidate area may be present in an area different from the correct position. According to these, there is concern that the accuracy of the template matching is lowered.

2. Next, there is another problem caused by the occurrence of a change in the form of an organ or a change in the section accompanying the respiration according to the elapse of time. The problem is a change in the positional relation between a peripheral organ and a tracking target. The in vivo motion tracking device 1 according to the first or second embodiment is assumed to be applied to an actual RFA operation environment. For this reason, it is necessary to track not a tumor changing according to cauterization but information of an organ positioned on the periphery thereof. For this reason, a positional relation between an organ used for a template and a tumor that is a tracking target changes due to a change in the form of the organ accompanied with the elapse of time or the like, and a tracking error is considered to occur regardless of a result of the template matching.

From such a reason, in a case where the update interval is short, it is difficult for an error to occur. On the basis of such results, next, for the conventional technique and the technique applying the in vivo motion tracking device 1 according to the first or second embodiment, results of actual tracking in a plurality of ultrasound moving images were compared with each other, whereby the effectiveness was verified.

<Tracking Experiment for Normal Liver Using Technique Applying In Vivo Motion Tracking Device 1 According to First or Second Embodiment>

In the in vivo motion tracking device 1 according to the first or second embodiment, a target organ is the liver, and thus, the tracking error was acquired for the normal liver as a target. Accordingly, the measurement of the tracking accuracy and the robustness of the technique applying the in vivo motion tracking device 1 according to the first or second embodiment was performed. By comparing with the conventional technique, the effectiveness of the technique applying the in vivo motion tracking device 1 according to the first or second embodiment was verified.

In a tracking experiment for an ultrasonic moving image, it is difficult to determine and track a target. The reason for this is that there are cases where it is difficult to continuously perceive an accurate position of a target due to a change in the section. From this, for an ultrasonic moving image captured such that the section does not change, correct coordinates are manually plotted, and a tracking error is acquired. In order to acquire an ultrasonic image such that the section does not change, the probe was placed to be in parallel with the direction of the motion. The liver greatly motions according to the respiration and thus is greatly influenced by the vertical motion of the phrenic. For this reason, capturing is performed in parallel with the direction of the vertical motion of the phrenic.

The section of a blood vessel was used as a tracking target. A blood vessel constantly has a fixed form in the condition that a change in the section does not occur and is appropriate as a target, and accordingly, the blood vessel was used.

In addition to the technique applying the in vivo motion tracking device 1 according to the first or second embodiment, tracking errors of four types of matching of a single template that is manually selected and a plurality of templates that are randomly selected, template matching using templates that are automatically selected according to the subspace method, and the update-type template matching that is the technique applying the in vivo motion tracking device 1 according to the first or second embodiment were measured.

[Moving Image for Learning and Accuracy Measurement Moving Image]

As a moving image for learning in the tracking experiment, a moving image similar to that used in a parameter identification experiment was used. Four types of moving images are acquired at the interval of 20 frames for a normal liver, and the tracking accuracy during 200 frames was measured for each frame. From this, learning was performed on the basis of a total of 97 images.

As the accuracy measurement moving image, six types of moving images were used. In a normal liver, ultrasonic moving images captured from the intercostal and the intercostal were used. An error of each moving image for 10 seconds was measured. In addition, for four particular types of moving images, additionally, errors for 30 seconds and 60 seconds were also measured.

[Technique Applying Vivo Motion Tracking Device 1 According to First or Second Embodiment]

In the update-type template matching, regarding the update timings, a total of four types of frame intervals at 2, 3, 4, and 7 frames for which the tracking result was good in the parameter identification experiment were applied. In addition, as a threshold for resetting the position of a tumor in the template matching using an initial template, a value acquired when the degree of correlation in the template matching was about 0.25 was used. The number of templates is 20, and the size of the template was 30 pixels×30 pixels (9 mm×9 mm). Here, this is the same size as the size of each block in the texture analysis using the HLAC. The total area of 20 templates is the same as the area of a smallest template among the areas of the templates in manual selection of templates to be described below. In the case of more templates, while it allows tracking on the basis of more characteristics, there is a problem in that the amount of calculation increases. For this reason, the number of templates is used for forming a condition equivalent to that of templates according to manual selection and decreasing the amount of calculation.

[Manual Selection of Template]

Figure 22:
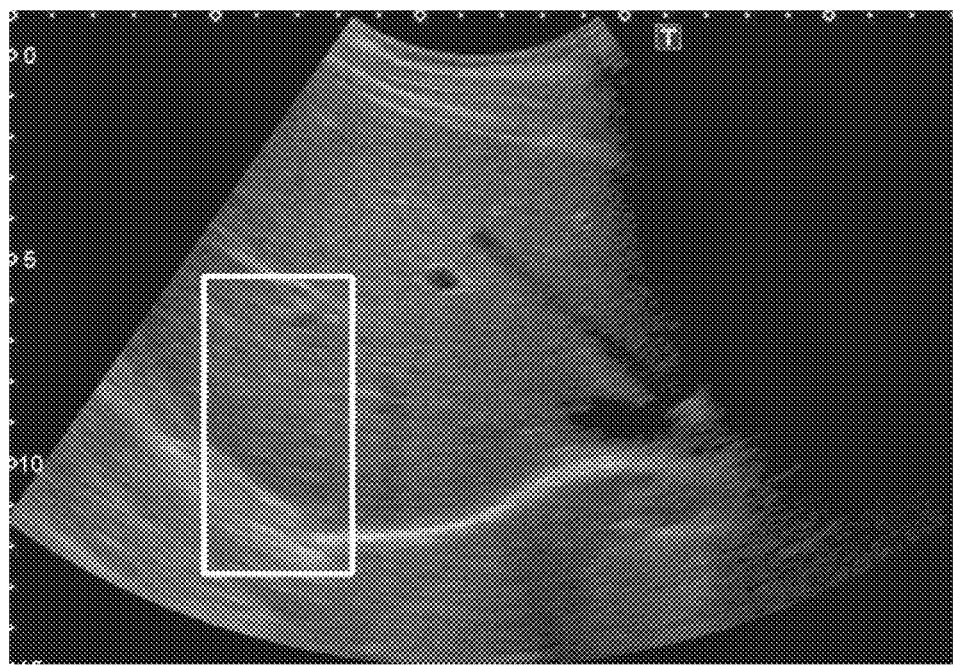
FIG. 22 is a diagram showing manual selection of a template.

FIG. 22 is a diagram showing manual selection of a template.

Figure 23:
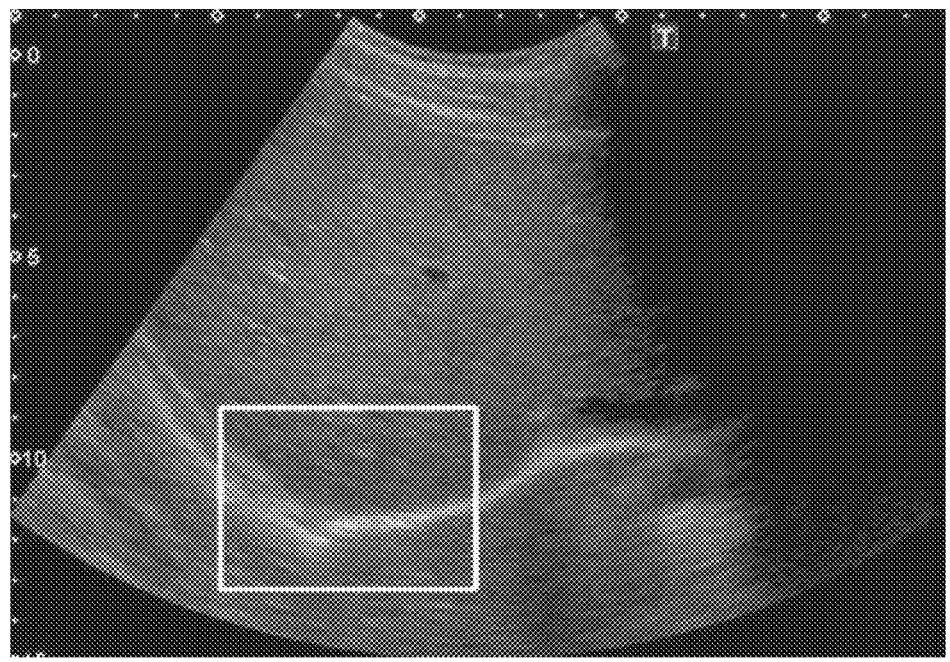
FIG. 23 is a diagram showing manual selection of a template.
Figure 24:
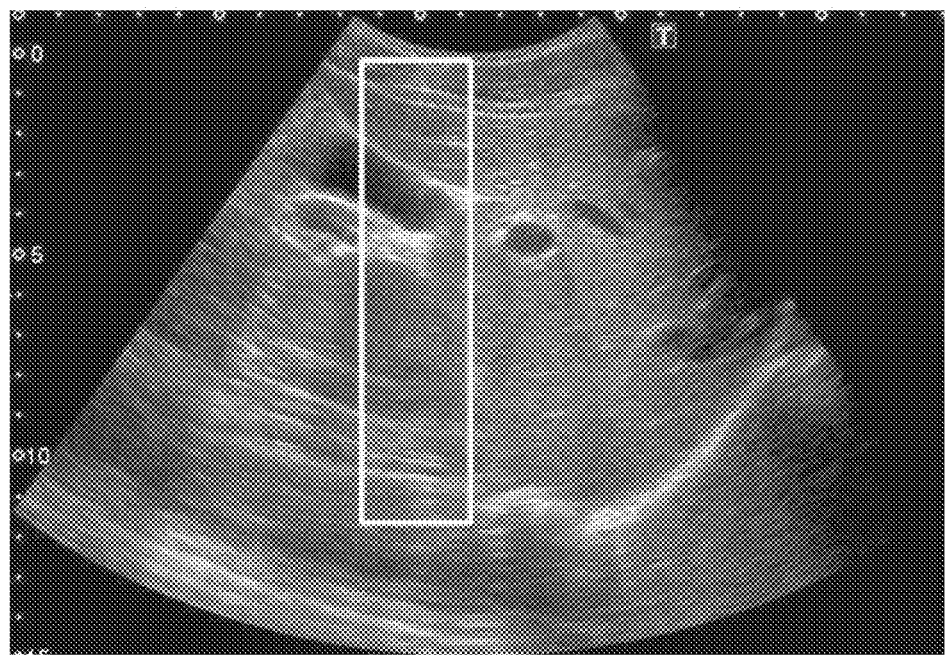
FIG. 24 is a diagram showing manual selection of a template.

A template to be selected in the tracking experiment according to manual selection of a template that is a conventional technique is selected in consideration of the following points. A template in consideration of each thereof is as shown in FIGS. 22 to 24.

- A diaphragm or a blood vessel that is anatomically characteristic is selected (see FIG. 22).
- A boundary portion of the liver, particularly, a characteristic portion having a high curvature is selected (see FIG. 23).
- On the boundary of the liver, a template is selected to traverse the skin side and the diaphragm side (see FIG. 24).
- A template is selected not to include a blood vessel that is a tracking target.

While being attentive for these, the tracking using a template that is manually selected was performed using four templates for each moving image.

[Random Selection of Template]

In order to check the effectiveness of automatic selection of a template using the proposed technique (the technique applying the in vivo motion tracking device 1 according to the first or second embodiment), templates of the same number as that according to the proposed technique and the same size as that according to the proposed technique were randomly selected, and tracking was performed. Similar to the proposed technique, 20 templates having a size of 30 pixels×30 pixels (9 mm×9 mm) were used. In addition, similar to the proposed technique, regarding the update of the templates, the templates were randomly selected.

[Result]

First, tracking errors at 10 seconds are as represented in the following Table 1. Here, the tracking errors at 10 seconds are tracking errors for six types of moving images. Here, "Automatic" represents automatic selection of templates using the subspace method, and "Manual" represents manual selection. Among them, the average of all is represented as "Average", and a case where particularly good results are collected is represented as "Champion". "Random" is a case where templates are randomly selected instead of using the subspace method. In addition, "Ada" represents that an update is performed.

TABLE 1

| | Proposed Technique | Automatic | Manual (Average) | Manual (Champion) | Random | Ada Random |
|---|---|---|---|---|---|---|
| Average error [mm] | 3.30 | 5.14 | 6.5 | 3.62 | 6.6 | 4.34 |
| Standard Validation [mm] | 2.39 | 5.28 | 11.3 | 2.67 | 6.02 | 4.75 |

The tracking errors at the next 30 seconds are as represented in the following Table 2. Here, the tracking errors at 30 seconds are tracking errors for six types of moving images.

TABLE 2

| | Proposed Technique | Automatic | Manual (Average) | Manual (Champion) | Random | Ada Random |
|---|---|---|---|---|---|---|
| Average error [mm] | 3.12 | 6.30 | 7.42 | 4.02 | 6.31 | 5.84 |
| Standard Validation [mm] | 2.41 | 8.49 | 10.9 | 5.28 | 7.18 | 4.52 |

The tracking errors at the next 60 seconds are as represented in the following Table 3. Here, the tracking errors at 60 seconds are tracking errors for six types of moving images.

TABLE 3

| | Proposed Technique | Automatic | Manual (Average) | Manual (Champion) | Random | Ada Random |
|---|---|---|---|---|---|---|
| Average error [mm] | 4.74 | 10.2 | 10.6 | 6.03 | 9.19 | 10.4 |
| Standard Validation [mm] | 4.54 | 11.5 | 14.0 | 9.34 | 9.16 | 10.2 |

In addition, for the proposed technique (the technique applying the in vivo motion tracking device 1 according to the first or second embodiment), particularly among these, the appearances acquired when update is performed at 2, 3, 4, and 7 frames are as represented in Table 4. Here, when a comparison is made by changing the frame interval, the tracking errors for four types of moving images were measured and compared with each other.

TABLE 4

|  |  | 2 Frame | 3 Frame | 4 Frame | 7 Frame |
|---|---|---|---|---|---|
| 10 s | Average error [mm] | 2.69 | 2.81 | 2.96 | 2.83 |
|  | Standard Validation [mm] | 1.90 | 1.97 | 1.92 | 1.93 |
| 30 s | Average error [mm] | 3.05 | 3.12 | 3.52 | 3.87 |
|  | Standard Validation [mm] | 2.40 | 2.41 | 2.58 | 3.14 |
| 60 s | Average error [mm] | 4.88 | 4.74 | 5.74 | 6.73 |
|  | Standard Validation [mm] | 4.83 | 4.55 | 5.36 | 6.73 |

According to the experiment, results described above were acquired.

In addition, the tracking accuracy for each moving image according to the proposed technique was as represented in Table 5. First, tracking results at 10 seconds were acquired as below.

TABLE 5

|  |  | 2 Frame | 3 Frame | 4 Frame | 7 Frame |
|---|---|---|---|---|---|
| Moving image 1 | Average error [mm] | 1.73 | 1.92 | 2.65 | 2.84 |
|  | Standard Validation [mm] | 0.877 | 0.819 | 1.31 | 1.57 |
| Moving image 2 | Average error [mm] | 3.45 | 3.61 | 3.46 | 3.52 |
|  | Standard Validation [mm] | 2.89 | 3.05 | 2.90 | 3.03 |
| Moving image 3 | Average error [mm] | 2.50 | 2.52 | 2.54 | 1.88 |
|  | Standard Validation [mm] | 1.54 | 1.47 | 1.56 | 0.883 |
| Moving image 4 | Average error [mm] | 3.10 | 3.18 | 3.20 | 3.09 |
|  | Standard Validation [mm] | 1.13 | 1.29 | 1.29 | 0.924 |

At 30 seconds, the result was as represented in Table 6.

TABLE 6

|  |  | 2 Frame | 3 Frame | 4 Frame | 7 Frame |
|---|---|---|---|---|---|
| Moving image 1 | Average error [mm] | 2.20 | 2.47 | 4.14 | 5.60 |
|  | Standard Validation [mm] | 1.36 | 1.25 | 2.19 | 3.60 |
| Moving image 2 | Average error [mm] | 3.96 | 3.90 | 4.04 | 4.06 |
|  | Standard Validation [mm] | 3.98 | 4.16 | 4.16 | 4.32 |
| Moving image 3 | Average error [mm] | 2.88 | 2.93 | 2.67 | 2.55 |
|  | Standard Validation [mm] | 1.34 | 1.22 | 1.20 | 1.09 |
| Moving image 4 | Average error [mm] | 3.15 | 3.17 | 3.21 | 3.29 |
|  | Standard Validation [mm] | 1.29 | 1.36 | 1.26 | 1.28 |

Then, at 60 seconds, the result was as represented in Table 7.

TABLE 7

|  |  | 2 Frame | 3 Frame | 4 Frame | 7 Frame |
|---|---|---|---|---|---|
| Moving image 1 | Average error [mm] | 2.26 | 4.32 | 7.99 | 11.8 |
|  | Standard Validation [mm] | 1.34 | 2.29 | 4.72 | 7.82 |
| Moving image 2 | Average error [mm] | 4.04 | 6.21 | 6.63 | 6.07 |
|  | Standard Validation [mm] | 4.14 | 5.99 | 6.65 | 5.65 |
| Moving image 3 | Average error [mm] | 3.04 | 2.69 | 2.63 | 2.59 |
|  | Standard Validation [mm] | 1.27 | 1.15 | 1.21 | 1.05 |
| Moving image 4 | Average error [mm] | 3.17 | 5.77 | 2.59 | 6.42 |

TABLE 7-continued

|  |  | 2 Frame | 3 Frame | 4 Frame | 7 Frame |
|---|---|---|---|---|---|
| image 4 | Standard Validation [mm] | 1.33 | 5.73 | 1.05 | 6.56 |

Here, the target accuracy is 2 mm. Meanwhile, in the tracking result at 10 seconds, an accuracy of 3.30 mm was acquired for six types of moving images, and an accuracy of 2.69 mm was acquired for four types of moving images. In addition, at 30 seconds, an accuracy of 3.05 mm, and, at 6 seconds, an accuracy of 4.88 mm was acquired. Among the 2, 3, 4, and 7 frames, high tracking accuracies were acquired for an update interval of 2 and 3 frames.

[Analysis]

A case where templates are not updated for the tracking result will be considered. At this, templates that are automatically selected using the subspace method and templates that are randomly selected will be compared with each other. At 10 seconds, the accuracy is higher than that at the time when templates are randomly selected. On the other hand, in a case where tracking for 30 seconds was performed, the accuracy was equivalent to that of the random selection. In the case of tracking for 60 seconds, the accuracy of the case of the random selection was higher than that of the automatic selection.

From this, in a short time, it can be understood that the selection of templates that are appropriate for tracking using the subspace method effectively functions. The reason for this is considered to be tracking of a moving image for 10 seconds at the time of learning and the use of a region having a high average degree of correlation. In other words, the reason is considered to be learning of templates that are optimal for tracking for about 10 seconds and selecting of the templates. From this, the effectiveness of the selection of templates that are appropriate for tracking using the subspace method could be checked.

Figure 25:
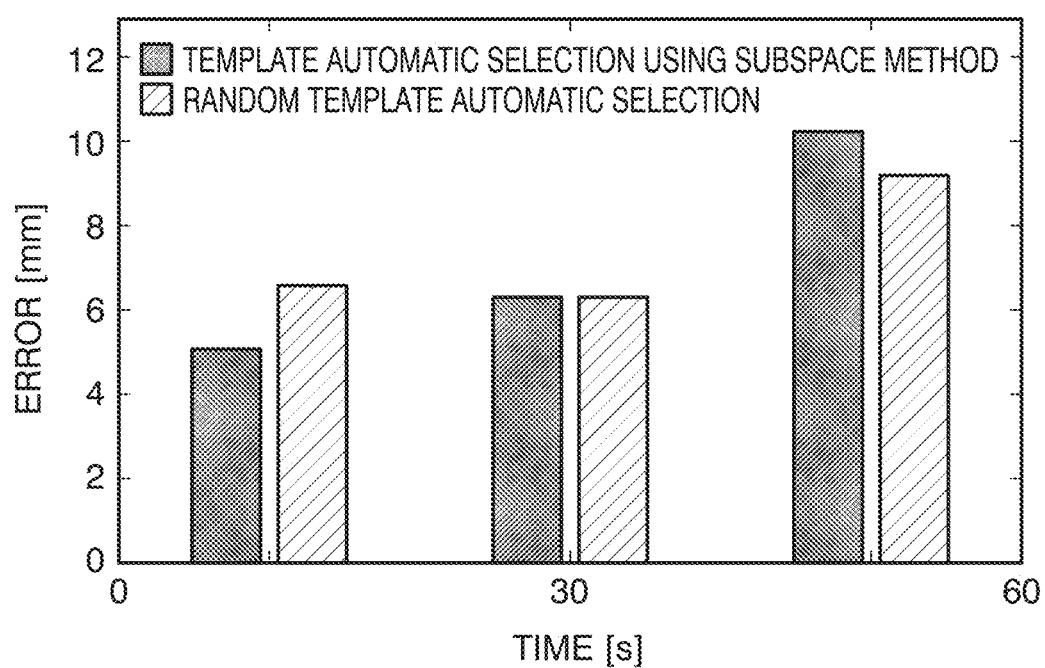
FIG. 25 is a diagram comparing automatic selection of templates using a subspace method and random selection of templates.

FIG. 25 is a diagram comparing automatic selection of templates using the subspace method and random selection of templates with each other. In more details, FIG. 25 represents an error of each frame when the frame is actually updated randomly.

The update-type template matching using automatic selection of templates using the subspace method, in other words, the proposed technique (the technique applying the in vivo motion tracking device 1 according to the first or second embodiment) was compared with a case where templates are randomly selected, and, as shown in FIG. 25, the accuracy of the proposed technique was higher than that of the case of the random template update at all the intervals of 10 seconds, 30 seconds, and 60 seconds. It is considered that the reason for this is in that, according to the proposed technique, an optimal template can be constantly selected in accordance with the update for every short time. From this, also in the case of being within 10 frames as at the time of update, it can be understood that selection of a template that is optimal for tracking using the subspace method effectively functions.

When the random selection of templates is compared with a case where update thereof is performed, update at 10 seconds and 30 seconds is effective, and the accuracy at the time of update is high. On the other hand, at 60 seconds, the accuracy of a case where update is not performed is higher than that that of a case where update is performed. It is considered that the reason for this is in that drift occurs in accordance with an accumulated error when the update is performed. As can be understood from FIG. 25, it can be understood that the error increases in accordance with the elapse of a time. As a reason for elimination of the accumulated error at the time of random selection not functioning well, there is a condition for resetting. It is considered that a condition for correcting the position of the in vivo motion is set according to the proposed technique, such a setting is used, and thus, the condition for improved correction is not matched.

Next, in the proposed technique (the technique applying the in vivo motion tracking device 1 according to the first or second embodiment), the effectiveness of update is considered as below. The accuracy of the proposed technique was compared with that of automatic selection using the subspace method. At this time, the accuracy of the proposed technique was higher than that of the case where update is not performed. From this, the effectiveness of the update of templates in the proposed technique could be checked.

Figure 26:
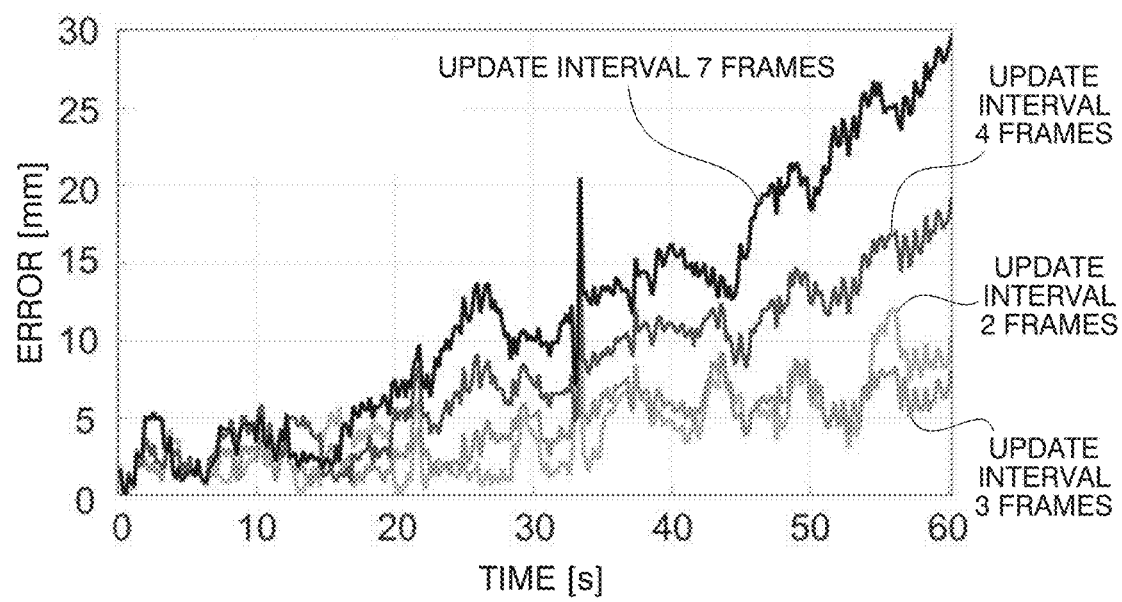
FIG. 26 is a diagram showing a tracking error in a moving image.
Figure 27:
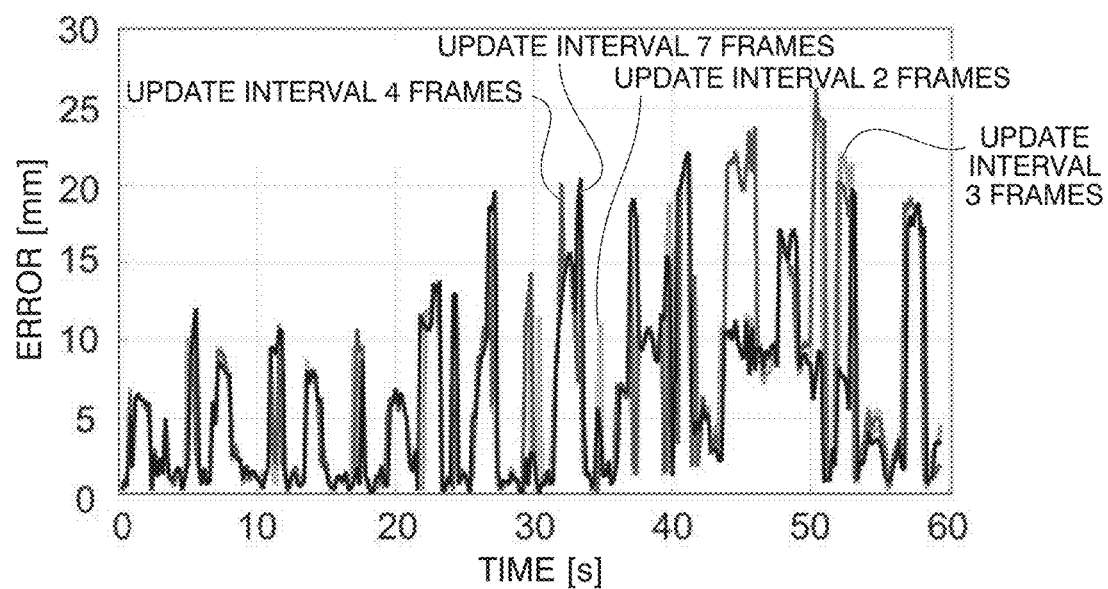
FIG. 27 is a diagram showing a tracking error in a moving image.
Figure 28:
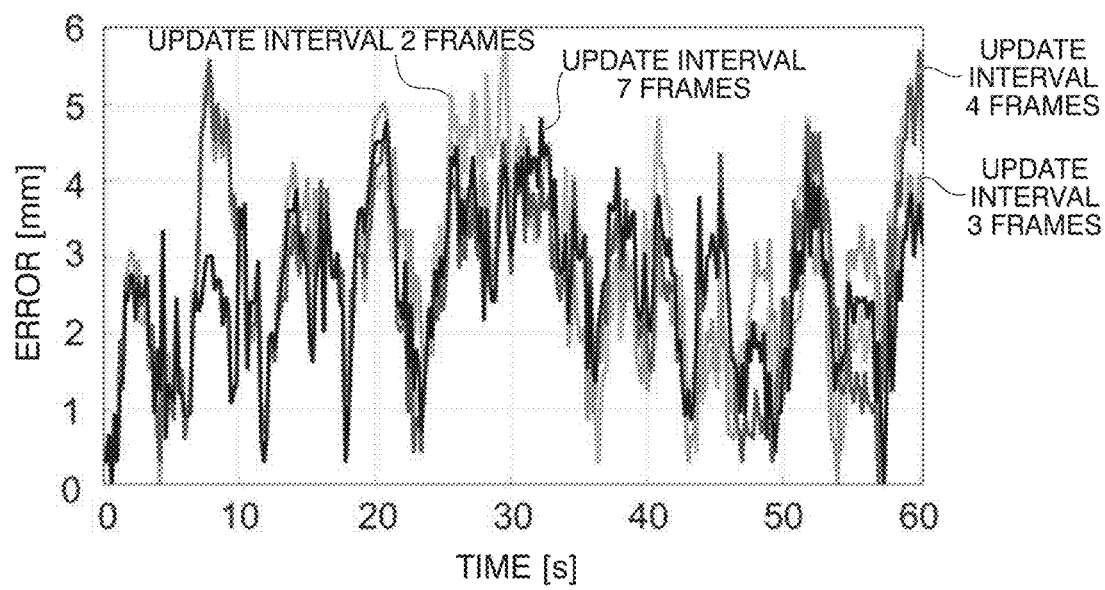
FIG. 28 is a diagram showing a tracking error in a moving image.
Figure 29:
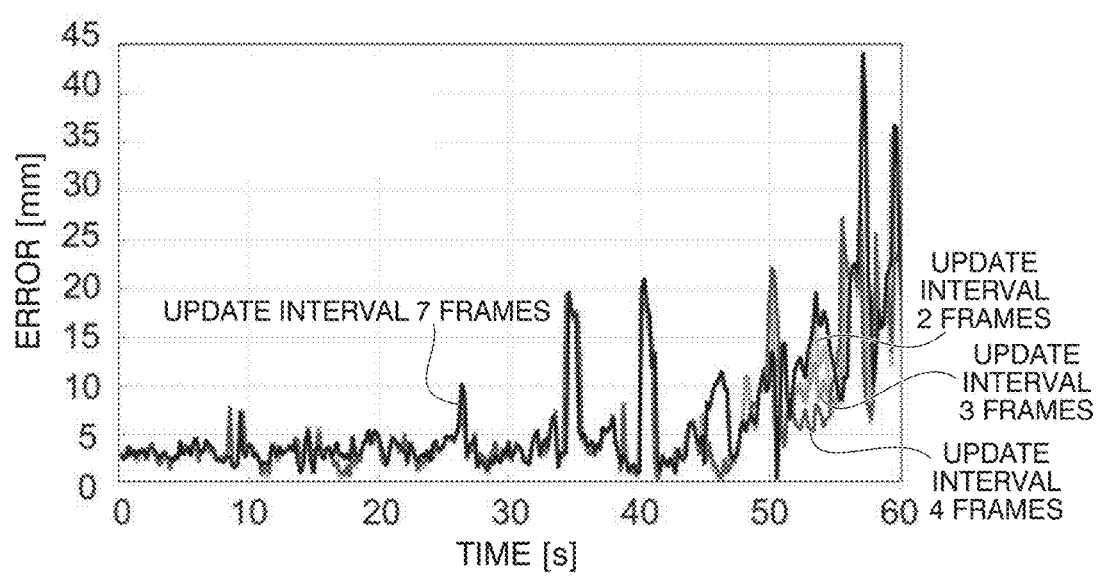
FIG. 29 is a diagram showing a tracking error in a moving image.

FIG. 26 is a diagram showing a tracking error in a moving image 1. FIG. 27 is a diagram showing a tracking error in a moving image 2. FIG. 28 is a diagram showing a tracking error in a moving image 3. FIG. 29 is a diagram showing a tracking error in a moving image 4.

For the four types of moving images, errors for 60 seconds are shown as graphs in FIGS. 26, 27, 28, and 29. From such graphs, it can be understood that there is a case where drift occurs and a case where drift does not occur in each moving image. As a case in which drift does not occur, the moving image 3 is present. Here, it can be understood that the error is small when compared with the other ultrasonic moving images. In addition, it can be understood that the error is small in all the 2, 3, 4, and 7 frames. Meanwhile, it can be understood that drift occurs in the moving image 1. In the 3, 4, and 7 frames, drift occurs from about 15 seconds. In the 2 frames, drift occurs from about 30 seconds. In addition, it can be understood that, near 60 seconds, the error becomes large as the update interval increases. From this, it is considered that the accumulated error occurs more as the update interval is increased. The reason for this is that, as the update interval is increased, a change in the positional relation between the template and the tracking target occurs, and thus, the error becomes larger. From this, it is considered that, by repeating the update of templates in a state in which the error occurs, and accordingly, the accumulated error becomes larger.

The errors in the moving image 2 and the moving image 4 are as shown in FIGS. 27 and 29. The appearance can be checked in which in the whole moving image 2 and near 35 seconds and 40 seconds in the moving image 4, the errors abruptly increase and thereafter abruptly decrease. This is caused by the position correcting process for eliminating the accumulated error not functioning well. As a position correcting process for eliminating the accumulated error, a technique using a tracking result using the initial template in which no accumulated error is present is used in the in vivo motion tracking device 1 according to the first or second embodiment. Meanwhile, in such ultrasonic moving images, in a case where tracking is not performed well for the initial template, the position is corrected on the basis thereof. Accordingly, it is considered that a large error occurs. Since the reset timing of the template is not appropriate, this problem occurs. In the in vivo motion tracking device 1 according to the first or second embodiment, the timing for correcting the position of the template is determined on the basis of the degree of correlation in the initial template. Then, as the threshold, a fixed value set in advance is used.

Figure 30:
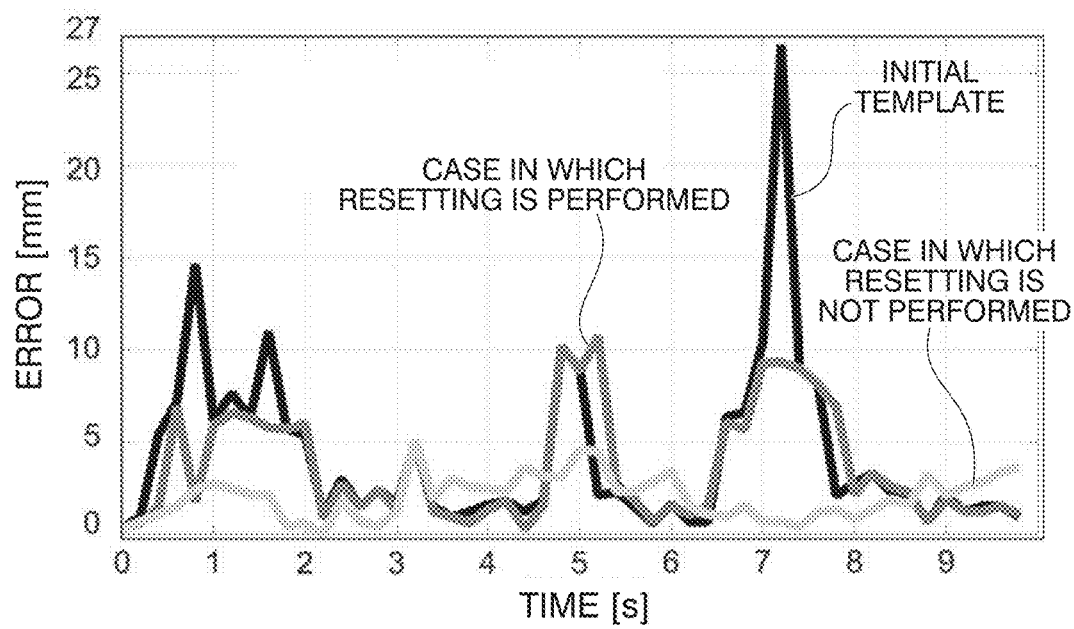
FIG. 30 is a diagram showing appearances of a case in which reset is used and a case in which reset is not used.

FIG. 30 is a diagram showing appearances of a case where reset is used and a case where reset is not used.

Near 1 seconds, 5 seconds, and 7 seconds, the error in the initial template and the error of a case where the accumulated error correction is performed are large. At this time, the error in a case where correction is not performed for the accumulated error is small. On the other hand, near 3, 6, and 9 seconds, an error in a case where the accumulate error is corrected is smaller than that in a case where the correction is not performed. In the former case, it can be understood that the accumulated error correction functions erroneously. In the latter case, it can be understood that the accumulated error correction effectively functions, which leads to improvement of the accuracy.

From this, it can be understood that, in the viewpoint of improvement of the tracking accuracy, the accuracy highly depends on the tracking error correction. When the accumulated error correction does not function well, and the position is corrected in a state in which an error is present in the initial template, the accuracy greatly deteriorates. It can be understood that this error greatly lowers the accuracy in the tracking. On the other hand, when the accumulated error correction effectively functions, the accuracy is improved to be higher than that of a case where the correction is not performed. By adjusting the timing at which the accumulated error correction is performed more accurately, it is considered that the improvement of the accuracy can be expected.

In the technique applying the in vivo motion tracking device 1 according to the first or second embodiment, the effectiveness could be checked in the tracking of the liver of a person through two experiments. Meanwhile, as a factor of the error, it could be checked that the error occurs in a portion at which the correction of the positional relation of the in vivo motion using the initial template for eliminating the accumulated error does not effectively function. The reason for this is that the degree of correlation of the template matching is not high only when tracking is correctly performed, and the height of the degree of correlation does not necessarily match the quality of tracking. From this, from now on, it is essential to determine a timing at which the correction of the positional relation of the in vivo motion is performed using a means observing the quality of tracking that is more robust.

In addition, it could be understood that, as the timing at which the template is updated, update is preferably repeated in a short period on the whole. Repeating the update of a template in a short period is considered to be appropriate for tracking an organ changing in the form in accordance with the respiration. In addition, as a factor causing that the tracking accuracy is high in a case where the template updating timing is a short period, there is another reason. The timing at which the positional relation of the in vivo motion is reset is only at the time of updating the template. Through the experiments described above, it could be understood that the tracking accuracy highly depends on the correction of the positional relation of the in vivo motion. From this, also a difference in the interval of the correction of the positional relation of the in vivo motion is considered to relate to a change in the error according to a difference in the interval of the update frame as a factor.

When compared with manual selection of templates that is a conventional technology, the proposed technique (the technique applying the in vivo motion tracking device 1 according to the first or second embodiment) is superior to the conventional technique in any aspect of the accuracy and the robustness. It is considered that the reason for this is that stable tracking is enabled in accordance with automatic selection of a template, the accuracy is improved by appropriately updating the template. Since the template can be automatically selected, templates can be sequentially selected in updating the template.

In addition, in the example in which the in vivo motion tracking device 1 according to the first or second embodiment is applied, as a factor lowering the accuracy, there is learning moving image. The learning data is 96 frames generated from the four moving images of this time, and similar scenes are considered to be learned much. By allowing the learning moving images to have more variations, further improvement of the system in the automatic selection can be expected. Also in moving images used for measuring accuracy, in a research performed by the inventors of the present disclosure and others, an ultrasonic moving image accompanying a change in the section and an abrupt motion was employed in consideration of the actual RFA treatment environment. When compared with an ultrasonic moving image having a uniform section, this is considered to easily cause the accuracy to deteriorate, and this is also considered to cause a numerical decrease in the accuracy.

Figure 31:
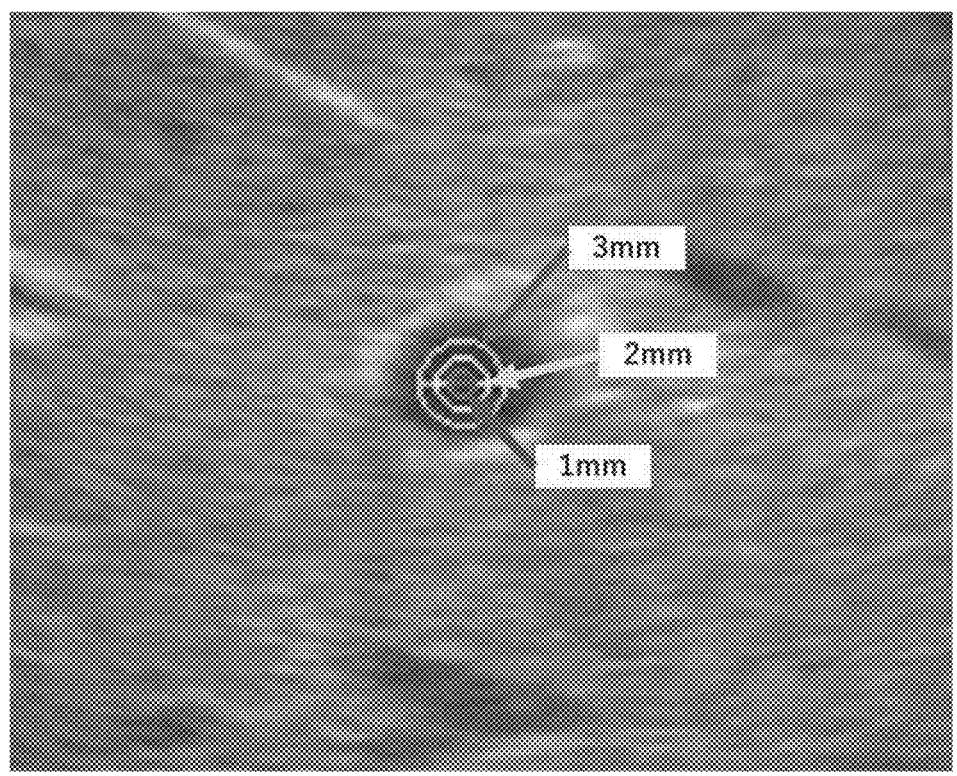
FIG. 31 is a diagram showing accuracy (an error of 1 mm, an error of 2 mm, and an error of 3 mm) of an ultrasonic image.
Figure 32:
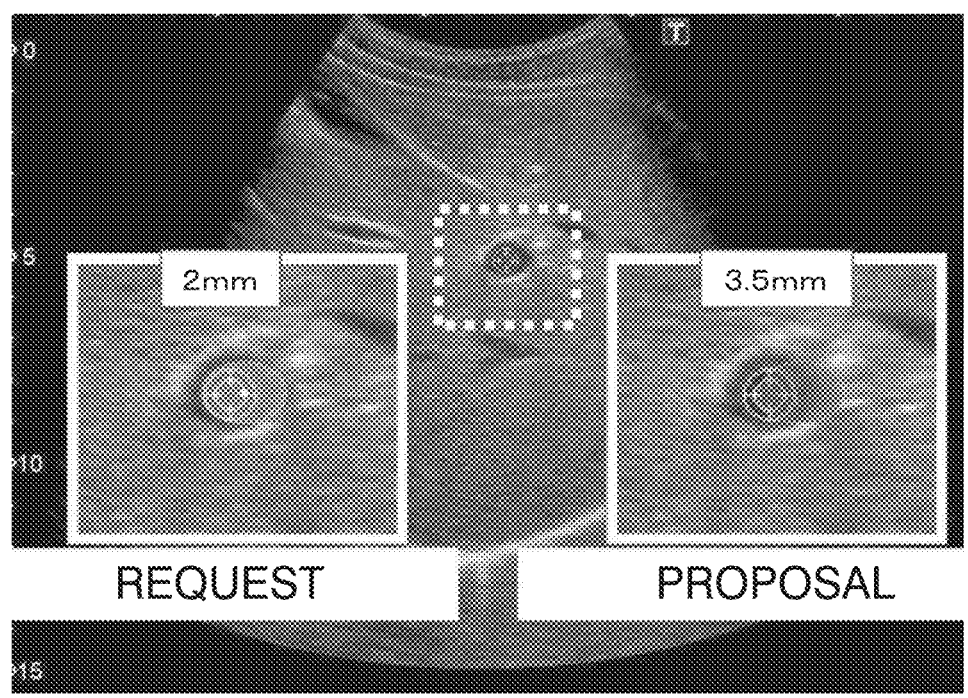
FIG. 32 is a diagram showing accuracy and the like according to a technique applying the in vivo motion tracking device according to the first or second embodiment.

FIG. 31 is a diagram showing accuracy (an error of 1 mm, an error of 2 mm, and an error of 3 mm) of an ultrasonic image. FIG. 32 is a diagram showing accuracy and the like according to the technique applying the in vivo motion tracking device 1 according to the first or second embodiment.

In the example shown in FIG. 32, highest accuracy was 2.26 mm. The requested accuracy is 2 mm at minimum and is ideally 1 mm. In addition, the accuracy acquired when the proposed technique (the technique applying the in vivo motion tracking device 1 according to the first or second embodiment) is used for six types of moving images of 10 seconds is 3.5 mm. In the moving images of 10 seconds, a moving image of which the section greatly changes is newly added, and the accuracy is considered to be lowered. At this time, the ratio per time being within the requested accuracy was 34%.

In order to perform tracking with the requested accuracy, the timing at which the position of the in vivo motion is corrected is considered to be important. According to enhancement of the algorithms, improvement of the tracking accuracy is expected.

From the viewpoint of performing correction using the initial template, the initial template needs to be strong. From that, for the initial template, a learning moving image is separately prepared, and a region for which the tracking accuracy is not easily lowered also for a long period than the tracking accuracy of a short period is selected, whereby correction using the initial template is considered to be more effective.

In the proposed technique (the technique applying the in vivo motion tracking device 1 according to the first or second embodiment), various parameters such as the number of templates, an update timing, a correction timing, and the size of the templates are present. Thus, by performing update-type template matching through reinforcement learning in which tracking is performed by determining the current status on the basis of an input image and determining the parameters in a form appropriate for the current status, tracking is considered to be performed in a form that is more optimal.

As described above, in the in vivo motion tracking device 1 according to the first or second embodiment, update-type template matching is performed by performing advance learning using a texture analysis, performing automatic selection of a template using the subspace method on the basis thereof, and sequentially updating the template that is automatically selected.

According to the in vivo motion tracking device 1 of the first or second embodiment, compared with template matching using a template that is manually selected, which is a conventional technique, improvement of the accuracy and improvement of the stability can be achieved. From this, the effectiveness of each of the automatic selection of a template on the basis of the texture and the update-type template matching can be checked.

In other words, according to the in vivo motion tracking device 1 of the first or second embodiment, the accuracy of tracking of an in vivo motion in an RFA treatment supporting system can be improved.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An in vivo motion tracking device tracking an in vivo motion that is a tracking target included in an ultrasonic image, the in vivo motion tracking device comprising:
   an image acquiring unit that is configured to acquire an ultrasonic image;
   an advance learning unit that is configured to perform advance learning using the ultrasonic image as learning data; and
   a tracking unit that is configured to track a position of the tracking target in an ultrasonic image including the tracking target after the advance learning performed by the advance learning unit,
   wherein the advance learning unit includes:
   a learning template processing part that is configured to perform a template process using the ultrasonic image of the learning data;
   an area extracting part that is configured to extract an area included in the ultrasonic image of the learning data;
   a learning texture analyzing part that is configured to perform a texture analysis of the area extracted by the area extracting part; and
   a main component analyzing part that is configured to perform a main component analysis of a result of the texture analysis performed by the learning texture analyzing part, and
   wherein the tracking unit includes:
   a tracking texture analyzing part that is configured to perform a texture analysis of the ultrasonic image including the tracking target;
   a template automatic selecting part that is configured to select an image area that is appropriate for tracking the tracking target as a template on the basis of a result of the texture analysis performed by the tracking texture analyzing part and a result of the learning performed by the advance learning unit;
   a tracking template processing part that is configured to perform an update-type template process for each of a plurality of templates that are sequentially selected by the template automatic selecting part; and
   a tracking target position determining part that is configured to determine a position having a highest degree of correlation as the position of the tracking target on the basis of a result of the template process for the plurality of templates performed by the tracking template processing part.

2. The in vivo motion tracking device according to claim 1,
wherein the tracking unit further includes a position correcting part that is configured to perform position correction according to an initial template having no accumulated error, and
wherein the position correcting part is configured to, when matching for the initial template has a degree of correlation of a fixed value or more, correct the position of the tracking target to a position of the tracking target at that time point.

3. The in vivo motion tracking device according to claim 1,
wherein the tracking unit further includes a monitoring part that is configured to constantly monitor a region of interest, and
wherein the monitoring part includes:
a region setting part that is configured to set a template of an initial region of interest;
a calculation part that is configured to, after tracking, calculate a distance between the template of the initial region of interest set by the region setting part and a region of interest that is currently being tracked;
a determination part that is configured to determine whether or not the distance calculated by the calculation part exceeds a predetermined threshold; and
a notification part that is configured to perform notification with an alarm when the distance calculated by the calculation part exceeds the predetermined threshold.

4. The in vivo motion tracking device according to claim 3, wherein, when the distance calculated by the calculation part exceeds the predetermined threshold, the notification part is configured to perform the notification through the alarm and store an image of a corresponding region of interest in a database in a readable form.

5. The in vivo motion tracking device according to claim 1,
wherein the learning template processing part is configured to perform template matching using the ultrasonic image of the learning data, and
wherein the tracking template processing part is configured to perform update-type template matching.

6. The in vivo motion tracking device according to claim 1,
wherein the learning template processing part is configured to perform Kernerlized correlation filters (KCF) tracking using the ultrasonic image of the learning data, and
wherein the tracking template processing part is configured to perform the KCF tracking.

7. The in vivo motion tracking device according to claim 1, wherein the in vivo motion tracking device is for supporting an ultrasound-guided radio frequency ablation (RFA) treatment or a high intensity focused ultrasound (HIFU) treatment.

8. An in vivo motion tracking method for tracking an in vivo motion that is a tracking target included in an ultrasonic image, the in vivo motion tracking method comprising:
acquiring an ultrasonic image;
performing advance learning using the ultrasonic image as learning data; and
tracking a position of the tracking target in the ultrasonic image including the tracking target after performing the advance learning in the performing of the advance learning,
wherein the performing of the advance learning includes:
performing a template process using the ultrasonic image of the learning data;
extracting an area included in the ultrasonic image of the learning data;
performing a texture analysis of the area extracted in the extracting of the area; and
performing a main component analysis of a result of the texture analysis performed in the performing of the texture analysis, and
wherein the tracking of the position of the tracking target includes:
performing a texture analysis of the ultrasonic image including the tracking target;
selecting an image area that is appropriate for tracking the tracking target as a template on the basis of a result of the texture analysis performed in the performing of the texture analysis and a result of the learning performed in the performing of the advance learning;
performing an update-type template process for each of a plurality of templates that are sequentially selected in the selecting of the image area; and
determining a position having a highest degree of correlation as the position of the tracking target on the basis of a result of the template process for the plurality of templates performed in the performing of the update-type template process.

* * * * *